United States Patent
Söderlund et al.

(10) Patent No.: US 7,361,461 B2
(45) Date of Patent: Apr. 22, 2008

(54) METHOD AND TEST KIT FOR QUANTITATIVE DETERMINATION OF POLYNUCLEOTIDES IN A MIXTURE

(75) Inventors: Hans Söderlund, Espoo (FI); Reetta Satokari, Helsinki (FI); Kari Kataja, Espoo (FI); Kristiina Takkinen, Espoo (FI)

(73) Assignee: Valtion Teknillinen Tutkimuskeskus, Espoo (FI)

( * ) Notice: Subject to any disclaimer, the term of this patent is extended or adjusted under 35 U.S.C. 154(b) by 347 days.

(21) Appl. No.: 10/519,403

(22) PCT Filed: Jul. 4, 2003

(86) PCT No.: PCT/FI03/00544

§ 371 (c)(1),
(2), (4) Date: Jan. 4, 2005

(87) PCT Pub. No.: WO2004/005545

PCT Pub. Date: Jan. 15, 2004

(65) Prior Publication Data

US 2006/0035228 A1    Feb. 16, 2006

(30) Foreign Application Priority Data

Jul. 5, 2002    (FI) .................................. 20021325

(51) Int. Cl.
*C12Q 1/68* (2006.01)

(52) U.S. Cl. ........................................................ 435/6

(58) Field of Classification Search ..................... None
See application file for complete search history.

(56) References Cited

U.S. PATENT DOCUMENTS

| | | | |
|---|---|---|---|
| 4,898,951 A | 2/1990 | Symons | |
| 4,968,602 A | 11/1990 | Dattagupta | |
| 5,082,830 A | 1/1992 | Brakel et al. | |
| 5,200,313 A | 4/1993 | Carrico | |
| 5,633,134 A | 5/1997 | Shuber | |
| 5,714,386 A | 2/1998 | Roederer | |
| 5,807,682 A * | 9/1998 | Grossman et al. | 435/6 |
| 5,981,171 A | 11/1999 | Kuhns | |
| 6,043,031 A | 3/2000 | Köster et al. | |
| 6,136,531 A * | 10/2000 | Leying et al. | 435/6 |
| 6,268,144 B1 | 7/2001 | Köster | |
| 6,395,486 B1 | 5/2002 | Grossman | |
| 6,480,791 B1 * | 11/2002 | Strathmann | 702/20 |
| 2002/0119455 A1 | 8/2002 | Chan | |
| 2006/0286570 A1 | 12/2006 | Rowlen et al. | |
| 2007/0009954 A1 | 1/2007 | Wang et al. | |
| 2007/0031829 A1 | 2/2007 | Yasuno et al. | |
| 2007/0042400 A1 | 2/2007 | Choi et al. | |
| 2007/0042419 A1 | 2/2007 | Barany et al. | |

FOREIGN PATENT DOCUMENTS

| | | |
|---|---|---|
| WO | WO 99/37663 | 7/1999 |
| WO | WO 02/55734 A1 | 1/2002 |

OTHER PUBLICATIONS

Amann et al., 1990, Applied and Environ Microbiol, 56: 1919-1925.*
Chen-Liu et al., 1995, Genomics 30: 388-392.*
Mayrand et al., "Automation of Specific Human Gene Detection," *Clin. Chem.*, 36(12):2063-2071, (1990).
Syvanen et al., "Quantification of polymerase chain reaction products by affinity-based hybrid collection, National Library of Medicine (NML), file Medline, Medline accession No. 2849762;" *Nucleic Acids Res*, 16(23):11327-38 (1988), Abstract Only.
Tenhunen et al., "A solution hybridization method for quantification of mRNA determining the amount and stability of oncogene mRNA,", Genet. Anul. Tech. Appl. (8): 228 (1990) Abstract only.
Tenhunen et al., "A solution Hybridization Method for Quantification of mRNAs: Determining the Amount and Stability of Oncogene mRNA," *Genetic Analysis Techniques and Applications*, 7(8):229-233 (1990).
Zhang et al., "Reconstruction of DNA sequencing by hybridization," *Bioinformatics*, 19(1):14-21 (2003).
Olejnik et al., "Photocleavable peptide-DNA conjugates synthesis and applications to DNA analysis using MALDI-MS," *Nucleic Acids Research*, 27:4626-4631 (1999).
Isola et al., "MALDI-TOF Mass Spectrometric Method for Detection of Hybridized DNA Oligomers," *Analytical Chemistry*, 73(9):2126-2131 (2001).

* cited by examiner

*Primary Examiner*—James Martinell
(74) *Attorney, Agent, or Firm*—Arent Fox LLP

(57) ABSTRACT

The invention relates to a method and test kit for quantitative determination of the amounts or relative proportions of polynucleotides in a mixture. The invention enables assessment of dynamic variations in a mixed population of organisms using affinity aided solution hybridization. The test kit comprises organized pools of polynucleotide probes having approximately the same number of nucleotides, which are distinguishable using resolution enabling tags providing the probes with different sizes. The resolution enabling tags may simultaneously act as tracer, affinity or primer tags. The probes are allowed to hybridize with affinity tagged analyte polynucleotides. The result is hybrids, recoverable on separation aiding tools provided with counterparts of the affinity tag. After the quantitative release of the probes, the individual probes can be amplified and recorded. The method and test kit are useful for determining hygienic and epidemiologic situations and evaluating the effect of antibiotic treatment and sanitary measures.

22 Claims, 18 Drawing Sheets

Analysis assembly and plate sealing
- automated pipetting station
- thermal sealer Denaturation and hybridisation
- automated thermal block Affinity capture, washes and elution
- magnetic particle processor Buffer adjustment and addition of standards
- automated pipetting station Size identification and quantification of fragments
- analyzer with automated injection

Fig. 11

SEQUENCE LISTING

```
<160> NUMBER OF SEQ ID NOS: 18

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
```

```
gctgcctccc gtaggagt                                                      18

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
gcttcttagt cargtaccg                                                     19

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
gcttcttagt cargtaccga aaaa                                               24

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
ttatgcggta ttaatctrcc ttt                                                23

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acaatgccag ggtttgacaa tg                                                 22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aaagacatcg ggccatttgc                                                    20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttagcacgcc catgaagtgg                                                    20
```

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aggatgaaga tttcgtggac ttga                                          24

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aagctaccaa aggtggccct c                                             21

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aggcttctct cgtatcagct ctgt                                          24

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gccctctgac gacatgtcca g                                             21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
attggcgtgc gcgtaaatgt                                               20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gccccagaag aacaccctgt                                               20

```
<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
accggccaaa tcgattctca                                                      20

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgctaggcgc gccgtc                                                          16

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggatgcggcc gctctc                                                          16

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgctaggcgc gccgtcgccc tctgacgaca tgtccag                                   37

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggatgcggcc gctctcattg gcgtgcgcgt aaatgt                                    36
```

METHOD AND TEST KIT FOR QUANTITATIVE DETERMINATION OF POLYNUCLEOTIDES IN A MIXTURE

CROSS-REFERENCE TO RELATED APPLICATION

This application is a National Stage entry of International Application No. PCT/FI2003/000544, filed Jul. 4, 2003, the entire specification claims and drawings of which are incorporated herewith by reference.

THE TECHNICAL FIELD OF THE INVENTION

The present invention is related to a method and a test kit for carrying out a quantitative determination, in which the amounts or the relative proportions of more than one individual target polynucleotide sequence present are determined simultaneously from a mixture of polynucleotide sequences using a mixture of polynucleotide probes having approximately the same number of nucleotides. The method and the test kit enable the quantitative determination of dynamic variations, of a multitude of individual organisms as well as related subpopulations present in a sample containing a mixture of organisms, i.e. a target population. The invention is based on a quantitative affinity aided solution hybridization combined with resolution providing fractionation. The invention is closely related to the invention disclosed in the International patent application WO 02/055734, in which the individual polynucleotide sequences of the probe mixture have distinct and distinguishable sizes. In contrast to this, the recognizing probes of the present invention have approximately the same number of nucleotides. The method and the test kit are useful in health care, environmental research, pharmaceutical industry and food industry and are applicable for many other diagnostic, biotechnical and scientific purposes.

THE BACKGROUND OF THE INVENTION

The rapidly accumulating genetic information combined with combinatorial chemistry and bioinformatics allowing the handling of enormous amounts of information has created a demand for new more accurate methods, which allow the simultaneous and/or sequential studies of dynamic situations and variations in natural environments. Accordingly, totally new approaches for carrying out research in molecular biology, health care, epidemiology, pharmaceutical and food industry are required.

In health care as well as in pharmaceutical and food industry, especially, practicing physicians, environmental consults, industrial hygienists, safety officers, health inspectors, environmental consults, veterinarians and/or other persons working with or being responsible for the evaluations of possible health or epidemiologic risks have a need for new effective tools for assessing the effects of remedial, sanitary or other measures on whole populations of organisms. There is for example an increasing demand for methods and tools for assessing the effects of new and conventional treatment modalities, including sanitary and remedial measures.

Based on the accumulating information including availability of genetical key elements and the knowledge of their biological role and functions, new methods are continuously developed. A powerful new tool is the oligomer-chip technology. The common characteristic of the microarray techniques and the feature distinguishing it from the present invention is that the probes or the polynucleotide sequences used as reagents are immobilized or coupled to a solid carrier. The immobilization of the probes acts as a steric hindrance and prevents the hybridization to take place in a stochiometric fashion, thus, resulting in a low yield. The oligomer-chip technology allows simultaneous handling of an enormous amount of samples, but the results are not quantitative and do not allow quantitative comparison in a wide dynamic range.

The principles of affinity aided solution hybridization are well known and have been disclosed, for example, in the patents U.S. Pat. Nos. 6,136,531 and 4,968,602. DNA diagnostics and detection using mass spectrometric methods have been described, for example in the patent U.S. Pat. No. 6,043,031 and the International patent application WO 99/37663.

The patent U.S. Pat. No. 5,807,682 discloses a method, which applies affinity aided solution hybridization and fractionation for detecting one or more mutation sites in the same gene. Therefore, the probes are short oligonucleotide sequences, and the hybridization temperature is critical making it difficult to use a large number of probes simultaneously, since multiple probes are prone to have different melting temperatures. One or more of these probes identifying specific mutations sites are separated and identified by selectively modifying the probes with a synthetically produced uncharged polymer, which alters the charge/fractional drag, which enables the probes to move with different mobility rates in a non-sieving medium.

None of the methods mentioned above tackle the problem of providing a method for a quantitative determination of several different polynucleotides simultaneously.

In the International patent application WO 02/055734 a method and test kit for overcoming the problem of obtaining quantitative results is described. Said patent application discloses a method and a test kit, including the reagents for quantitative determination of polynucleotides or variations in their amounts in a cell or tissue sample. The method and test kit applies organized pools of soluble polynucleotide probes with distinct, distinguishable sizes varying from 16 to several thousands of base pairs. The quantitative method allows comparative assessment of variations, e.g. in transcription profiles or expression patterns. Said method is based on the varying and distinct sizes of soluble polynucleotide probes. It is the difference in size of the probes that enables the assessment of the individual nucleic acid sequences.

Probes from more or less conserved or hypervariable regions are known to enable classification and organization of different organisms in phylogenetic levels including groups, genus, species or subspecies. A quantitative evaluation of the amounts of individual organisms, their subpopulations in a mixture using said probes would enable studies of dynamic variation in target populations. Such evaluations would have several useful applications. Unfortunately, the method disclosed in WO 02/055734 is not applicable to probes, which are polynucleotide sequences having approximately the same number of nucleotides, because sufficient resolution for reading the results may not be achieved.

Consequently, the objective of the present invention is to provide a new and effective tool to enable specialists working with or being responsible for investigations and evaluations of possible health risks and the need of repair or other remedial measures to obtain quantitative data for evaluating the risks and remedies.

The objective of the present invention is to provide a method and test kits not only for quantitative determination of the amounts and relative proportions of individual organisms, or certain subgroups in a population, it also allows comparative assessments of sequential time variations in the population due to internal or inherent control mechanism taking place in the cell or selected measures or interventions externally applied on the organisms or populations of organisms or polynucleotides thereof. Comparative assessments of population in sample obtained from different sites may also be made by this method. Simultaneously, the objective is to provide a very sensitive test, which allows the quantitative determination of very small amounts of analyte polynucleotides, which otherwise would be under the detection limit. This is achieved by PCR-amplification of the probes, which correspond to the amount of analyte polynucleotides having a sequence complementary to that of the probe in the sample. Due to the fact that the probes are present in surplus as compared to the analyte polynucleotides they may be quantitatively recovered and released before the PCR-amplification.

The advantages related to the present invention as well as to the method and test kits described in WO 02/055734, include the fact that the quality of the polynucleotide preparation, especially RNA, to be analyzed, is not critical. For example, RNA known to require special treatment, due to its instability, may be used without adding any resolution enabling tags for the quantitative assessment. The manufacturing of test kits, which need not include immobilization steps and certain commercially available reagents allows preparation of easily adaptable tailor-made tests, directing the attention to certain subsets of genes in a given organism or related organisms.

The method may be used as fully automatic or semiautomatic assemblies. The procedure may be interrupted at several stages. The samples and reaction products may be preserved until sufficient data has been collected or it is more convenient to continue the process and record the results.

A SUMMARY OF THE INVENTION

As a summary, the present invention allows a simultaneous, quantitative recording of changes and variations of the amounts and/or relative proportions of more than one individual polynucleotide sequences in a mixture. The method and the test kit enable the determination of amounts and/or relative proportions of individual organisms or subgroups thereof from a sample or mixed population pool, which has been taken from different sites or at different points of time, before and after certain internal or external treatments or interventions. This is useful, especially, when studying the effects and the impact of various physical and chemical stimuli applied on the target population, including antibiotic treatment, hygienic measure and other interventions. The invention also allows the evaluation of inherent changes in population. The invention allows simultaneous comparative assessment of several biological phenomenons.

The method and test kit of the present invention are not only quantitative, they may also be made very sensitive and allow quantitative detection of polynucleotide sequences present in diminutive amounts. The characteristic features of the method and test kit of the present invention as well as their applications are as defined in the claims.

A SHORT DESCRIPTION OF THE DRAWINGS

Figure 1:
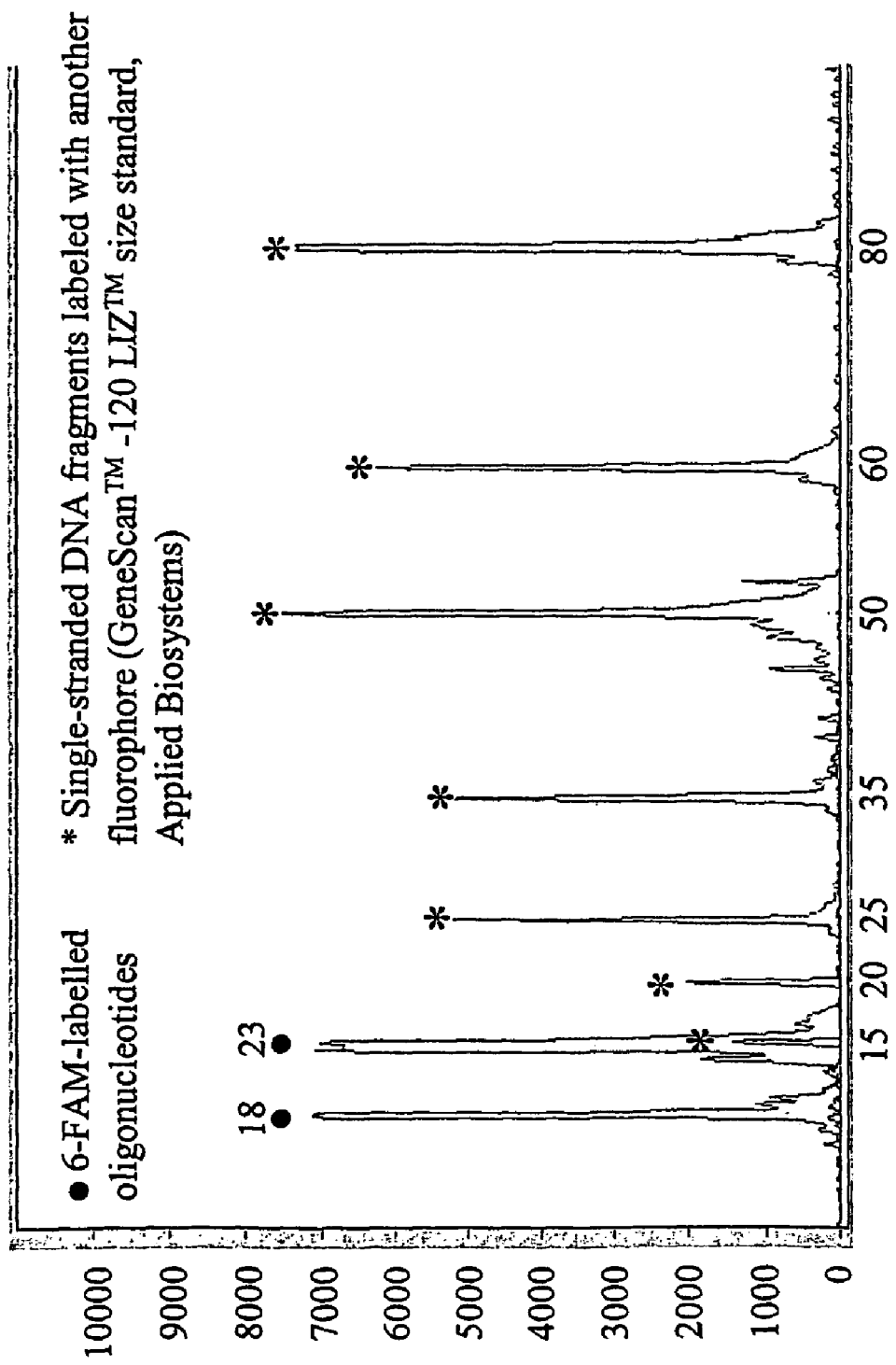
FIG. 1 shows the separation of single stranded DNA fragments and polynucleotides with different fluorophores by capillary electrophoresis.
Figure 2A:
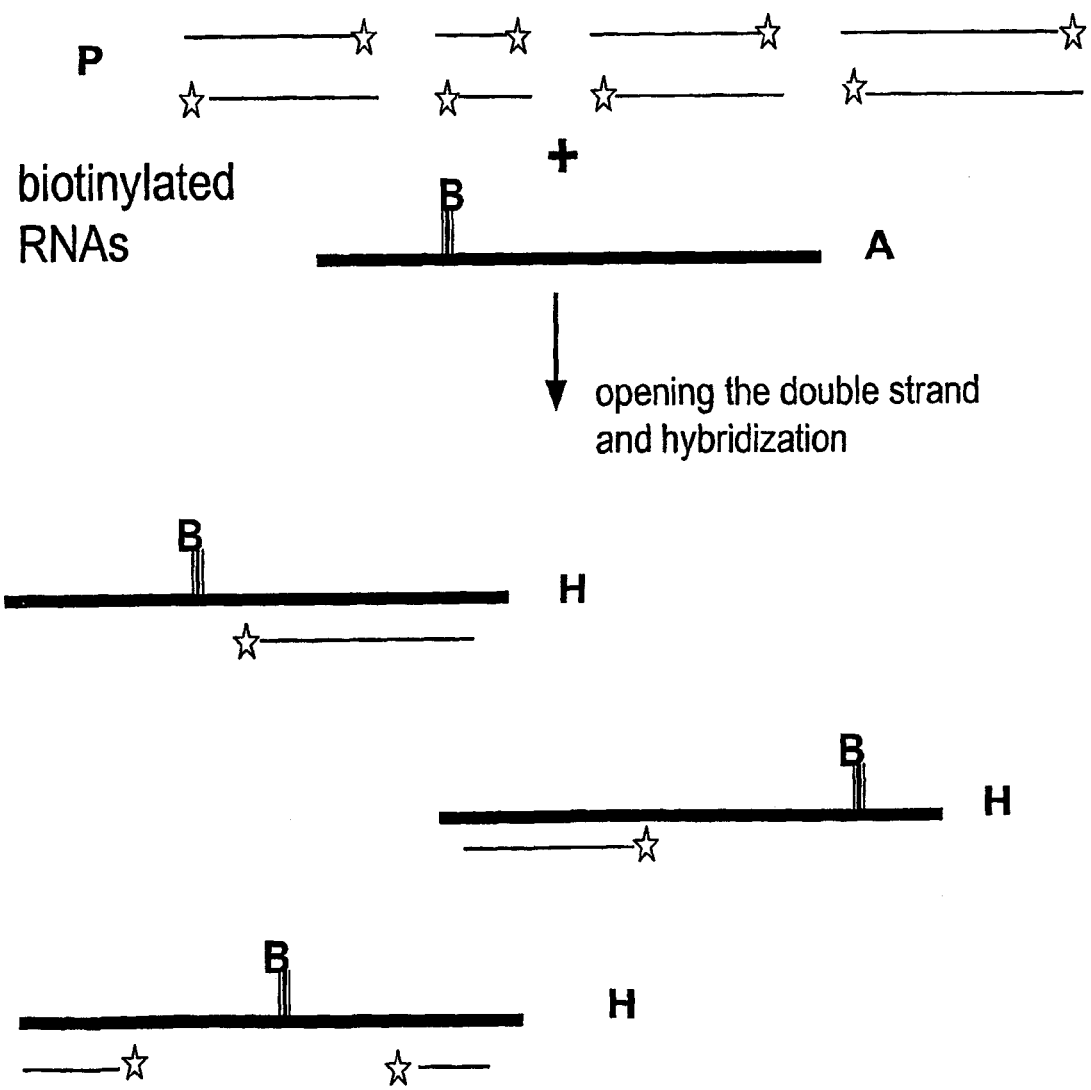
FIG. 2A illustrates the hybridization process between the tracer (star) tagged probes (P) and affinity or biotin (B) tagged single stranded RNA analyte sequences and the formation of hybrids (H) between the analytes (A) and the probes (P).
Figure 2B:
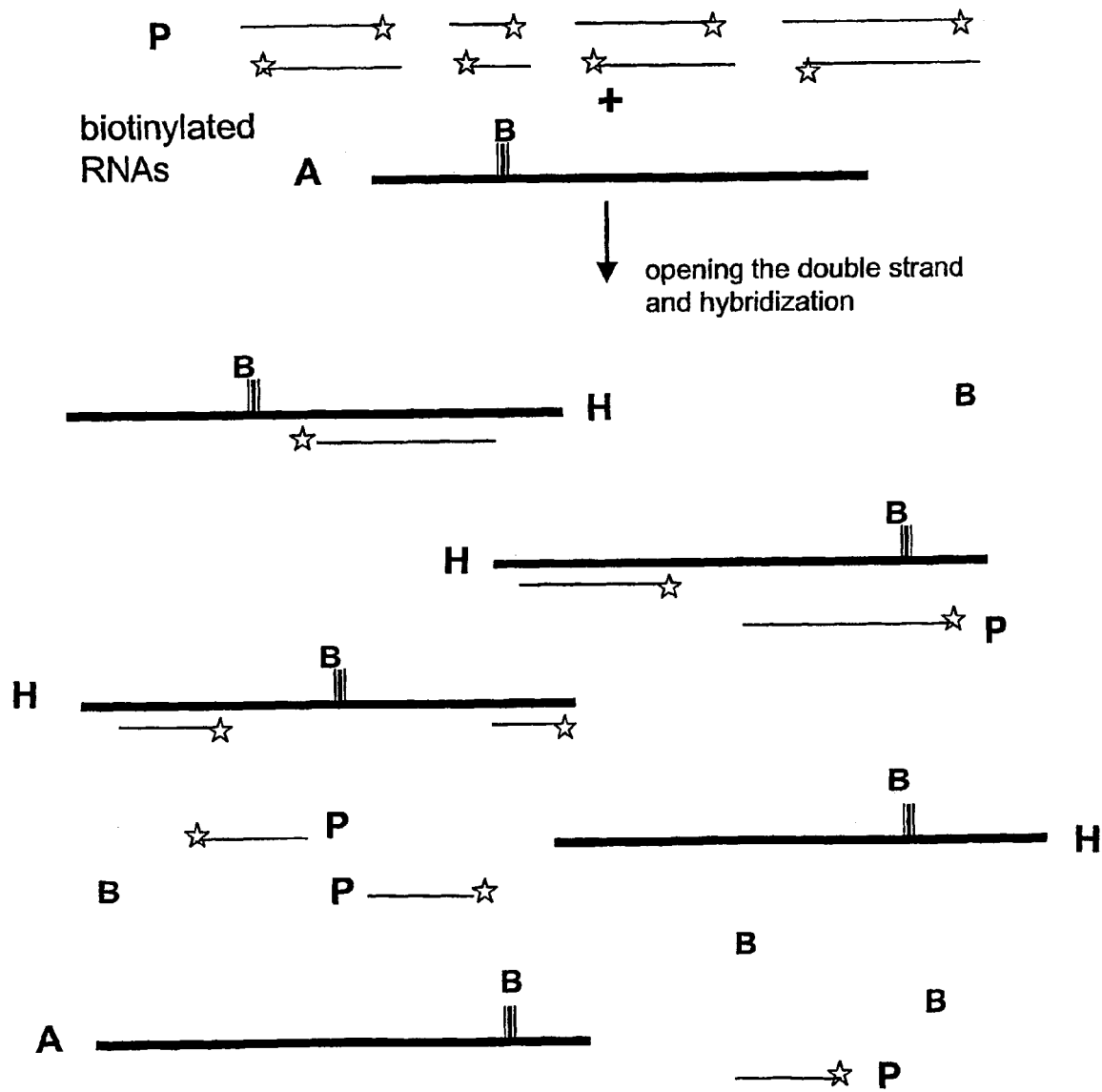

FIG. 2B illustrates the hybridization process between probes (P) with tracer tags (star) simultaneously acting as resolution enabling tags and affinity or biotin (B) tagged double stranded polynucleotide or RNA analyte sequences and the formation of hybrids (H) between the analytes (A) and the probes (P). Probes, which do not match analyte sequences, or which are present in molar excess, remain free in solution.

Figure 3A:
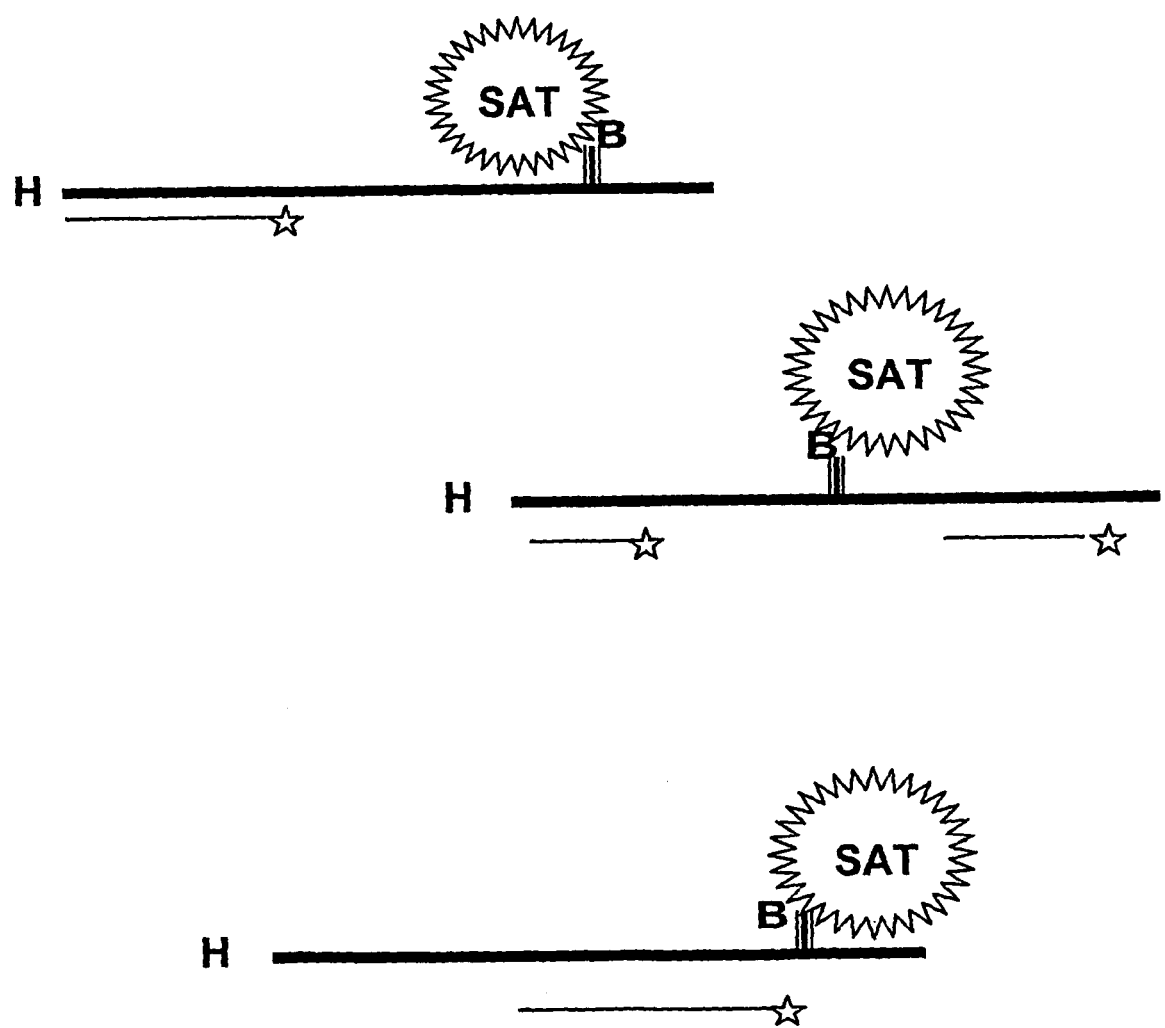

FIG. 3A depicts the capture of the affinity (B) tagged hybrids (H) to a solid separation aiding tool (SAT) covered with the counterpart of the affinity tag (B).

Figure 3B:
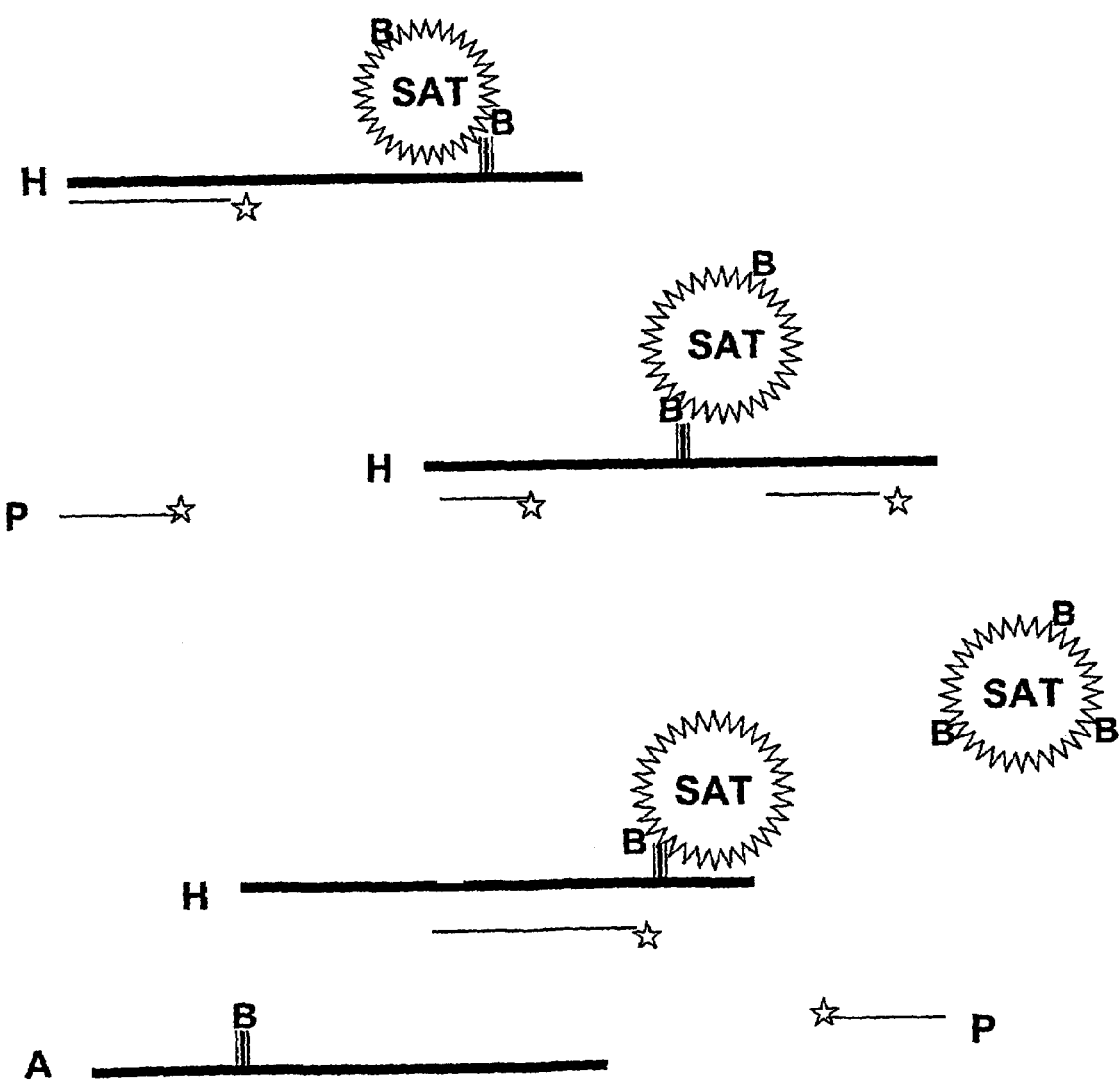

FIG. 3B depicts the capture of the affinity (B) tagged hybrids (H) to a solid separation aiding tool (SAT) covered with the counterpart of the affinity tag (B). Tracer tagged probe sequences, which have not hybridized with an affinity tagged analyte sequence, are not captured. Naturally, the separation aiding tools (SAT) bind free affinity tag as well as such affinity tagged analytes to which no probe sequence has hybridized.

Figure 4:
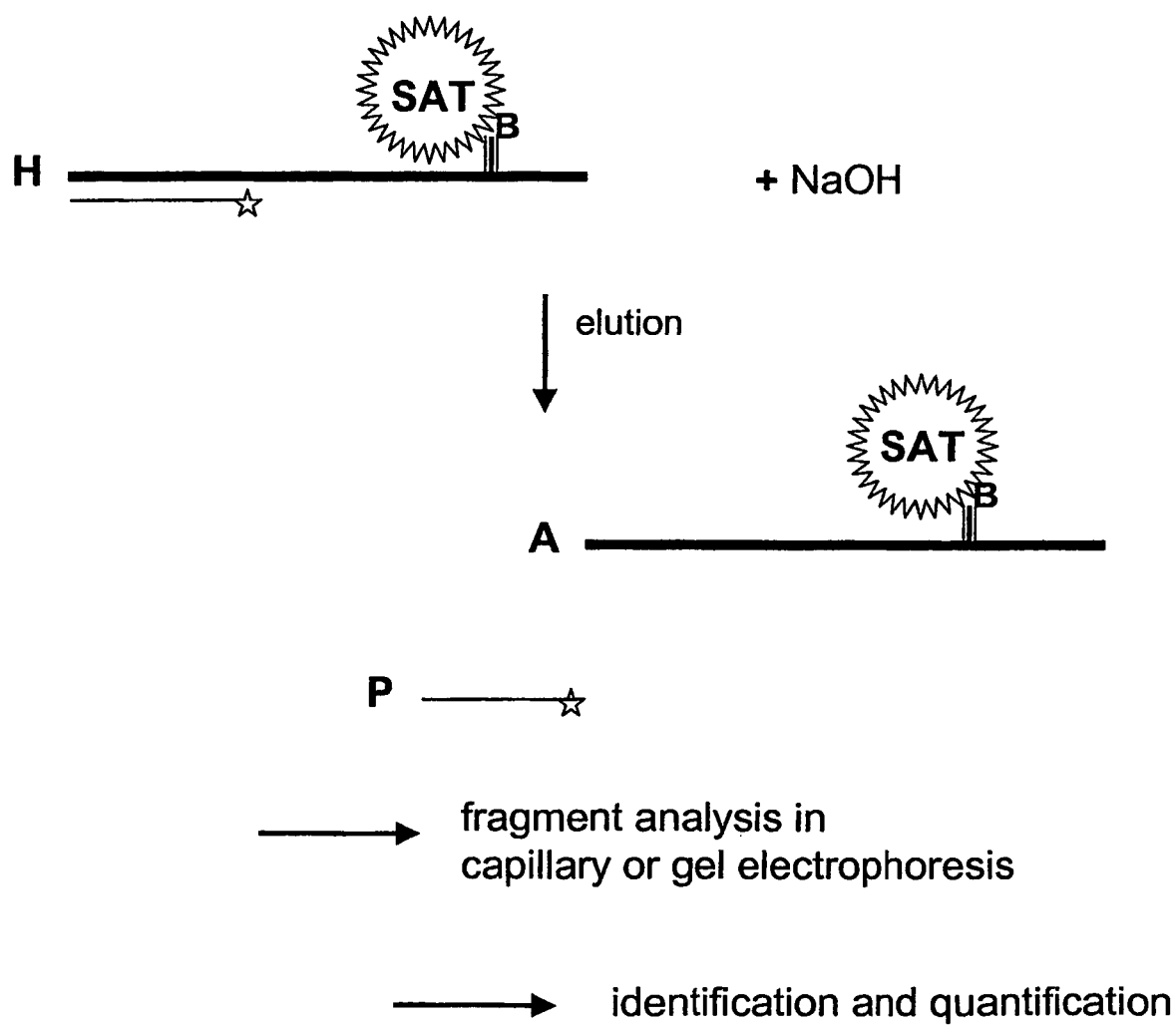

FIG. 4 depicts release using elution of the tracer tagged probes (P) from the solid separation aiding tool (SAT)/ leaving the affinity tagged analyte sequence (A) with the separation aiding tool (SAT) and tracer tagged probe (P) in solution.

FIGS. 5 A-B depict a 16S rRNA approach in microbial ecology.

Figure 5A:
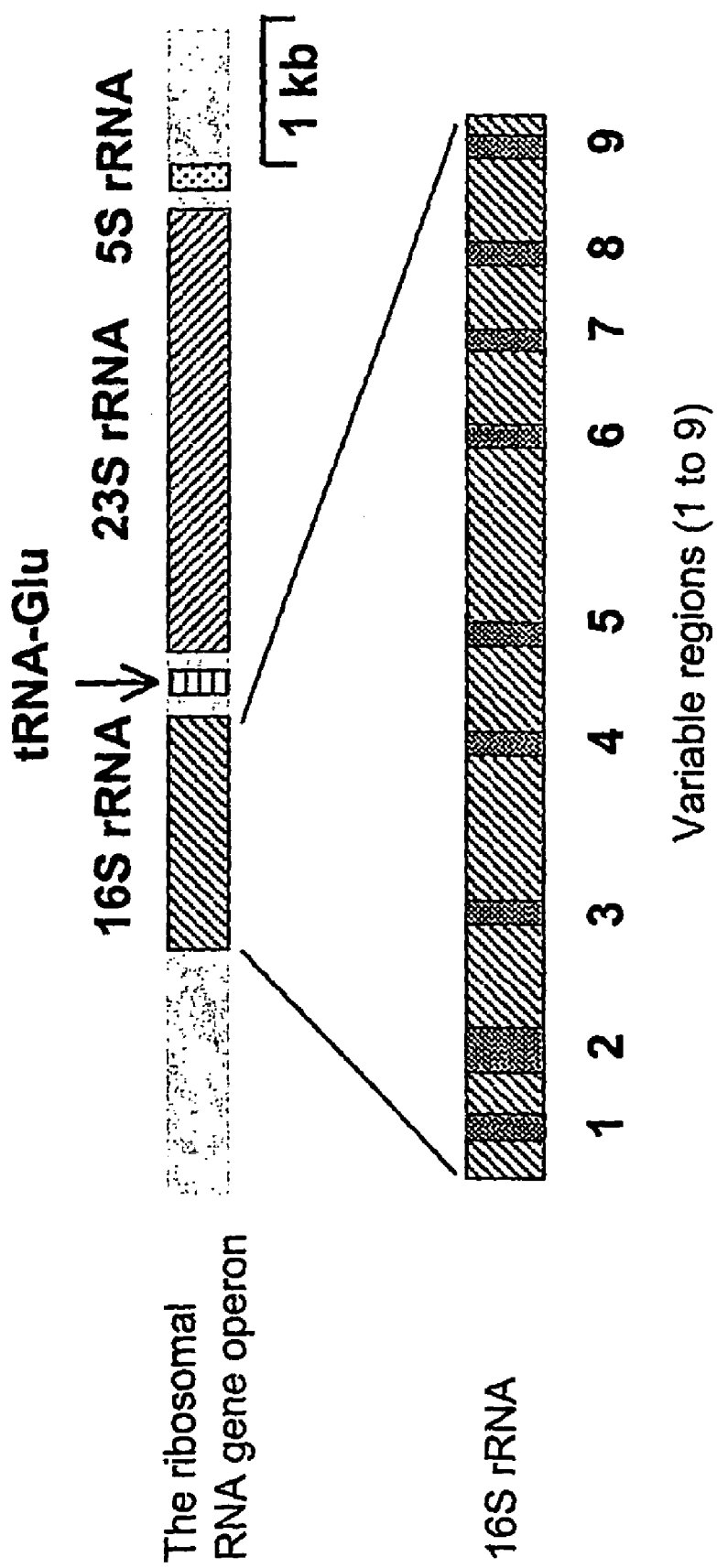

FIG. 5A depicts a ribosomal RNA gene operon including 16S, 23S and 5S rRNA with the variable regions 1-9 of the 16S rRNA highlighted.

Figure 5B:
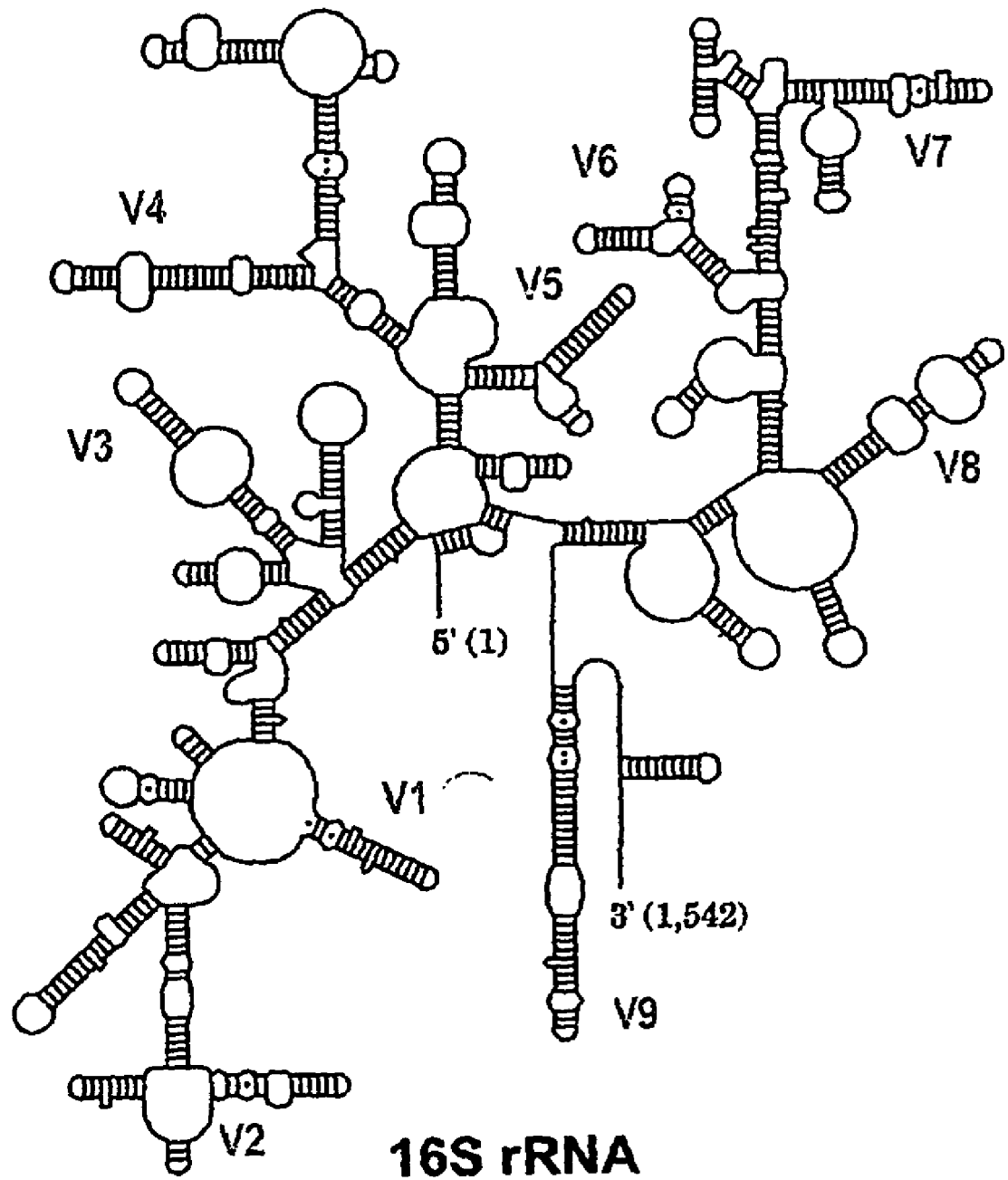

FIG. 5B depicts the structure of 16S rRNA with the variable regions allowing species identification and more or less conserved regions allowing identification of microbial groups.

Figure 6:
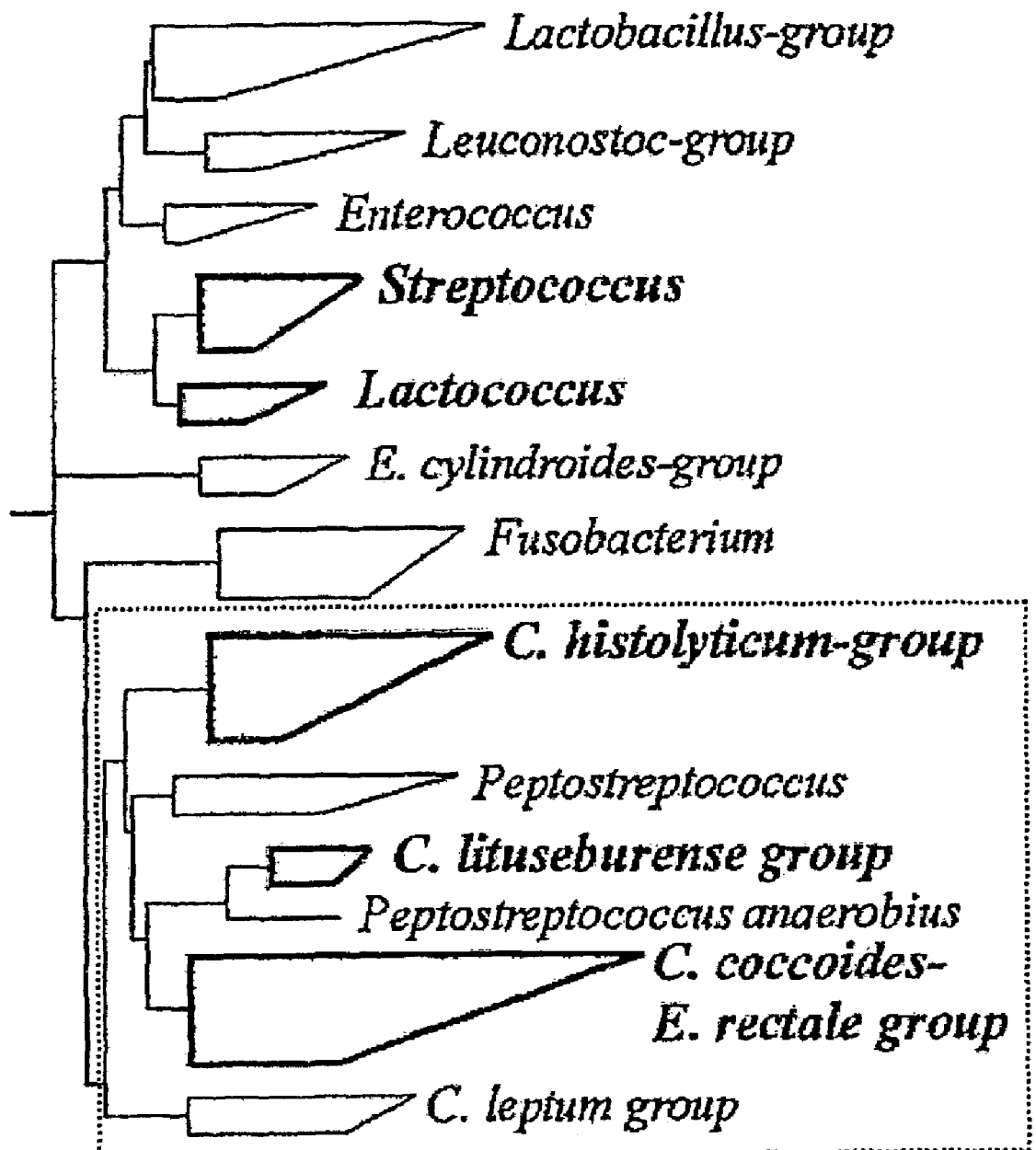

FIG. 6 depicts a phylogenetic tree of clostridia and related bacteria.

Figure 7:
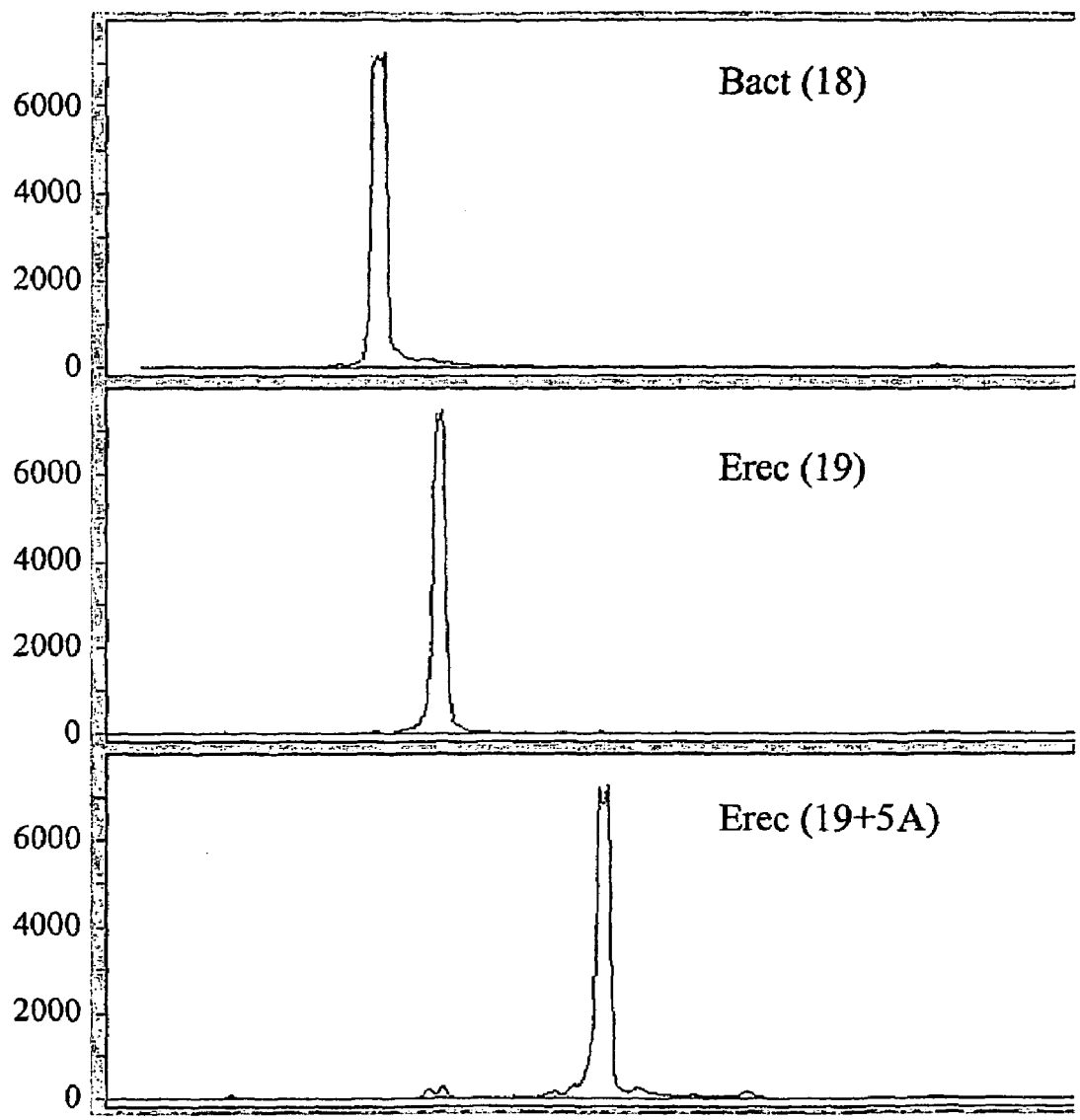

FIG. 7 shows the results, which may be recorded from an electropherogram and from a data file when carrying out the comparative process of the invention according to Example 1. All probes are functional in hybridization with *C. symbiosum* E981051 RNA. Bact and Erec probes have different sizes (18 and 19 bases, respectively) and different mobilities. The electrophoretic mobility of the Erec-5A probe is different from that of the Erec probe due to the addition of an A-tail.

FIGS. 8 A-B show the result, which may be recorded from an electropherogram and from a data file obtained when carrying out the comparative process of the invention according to Example 2.

Figures 8A, 8B:
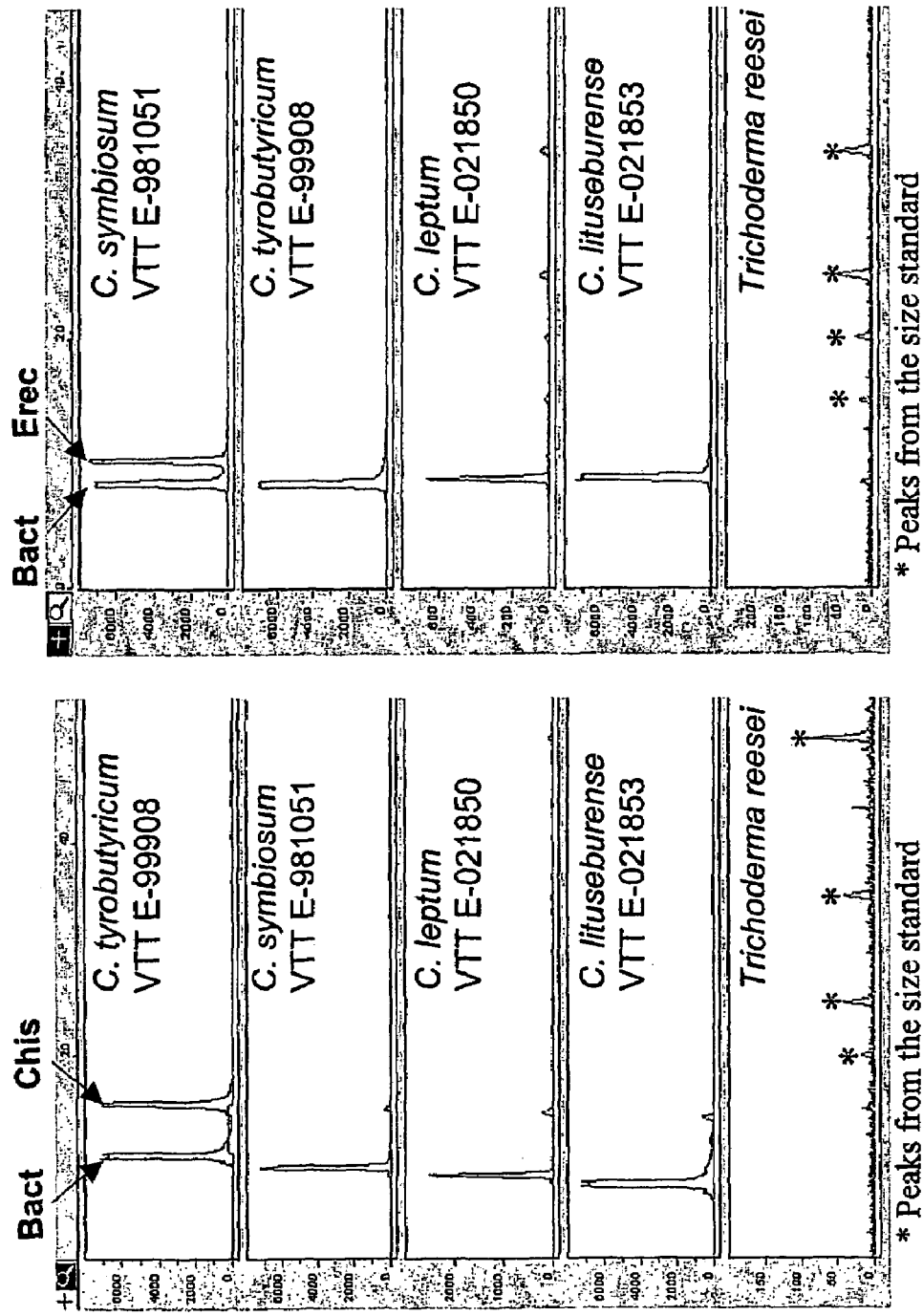

FIG. 8A shows the result with the probes Bact and Chis. Chis probe identifies only strain *C. tyrobutyricum* E99908, whereas Bact probe identifies all bacterial strains. Neither probe identifies fungus *Trichoderma reesei*.

FIG. 8B shows the result with the probes Bact and Erec. The Erec probe identifies only strain *C. symbiosum* E981051, whereas the Bact probe identifies all bacterial strains. Neither probe identifies the fungus *Trichoderma reesei*.

Figure 9:
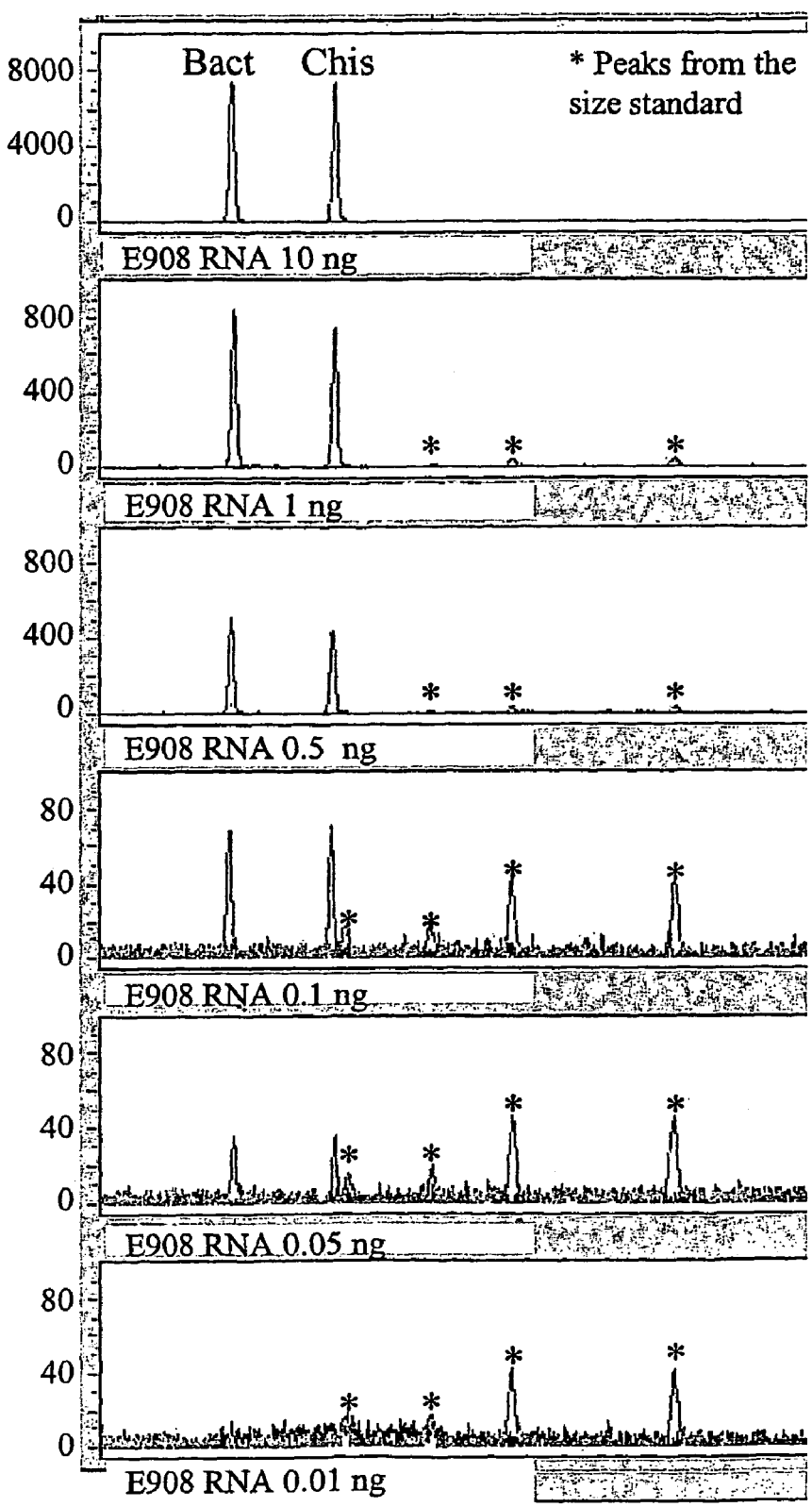

FIG. 9 shows the results, which may be recorded from an electropherogram and from a data file obtained when carrying out the quantitative process of the invention according to Example 3. The Bact and Chis probe signal intensities correspond to the amount of *C. tyrobutyricum* E908 RNA used for hybridization.

FIGS. 10 A-B show the results, which may be recorded from an electropherogram and from a data file when carrying out the qualitative and quantitative process of the invention according to Example 4.

Figure 10A:
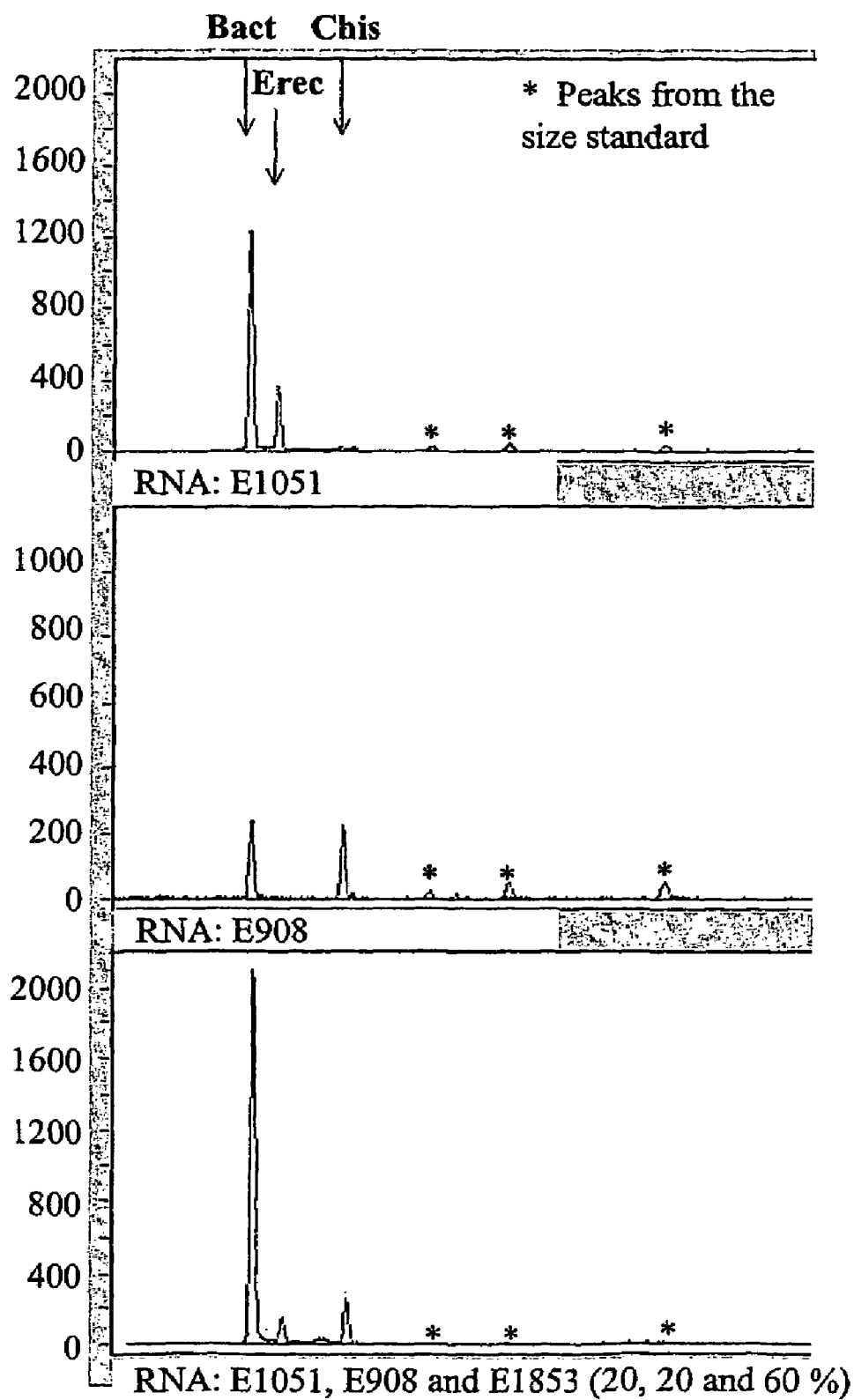

FIG. 10A depicts results obtained when analysing RNA from *C. symbiosum* E1051 with the probes Bact and Erec, RNA from *C. tyrobutyricum* E908 with the probes Bact and Chis, and a microbial population comprising RNA from *C. butyricum* E908, *C. symbiosum* E1051 and *C. lituseburense* E1853 with probes Bact, Chis and Erec. The Bact probe identifies all strains, whereas the Chis probe identifies only strain E908 and the Erec probe identifies only strain E1051. The level of fluorophores, which label the probes Bact and Chis is equal, whereas that of the probe Erec is lower. The proportion of RNA from each strain is given as percentage of the total RNA used for the hybridization.

Figure 10B:
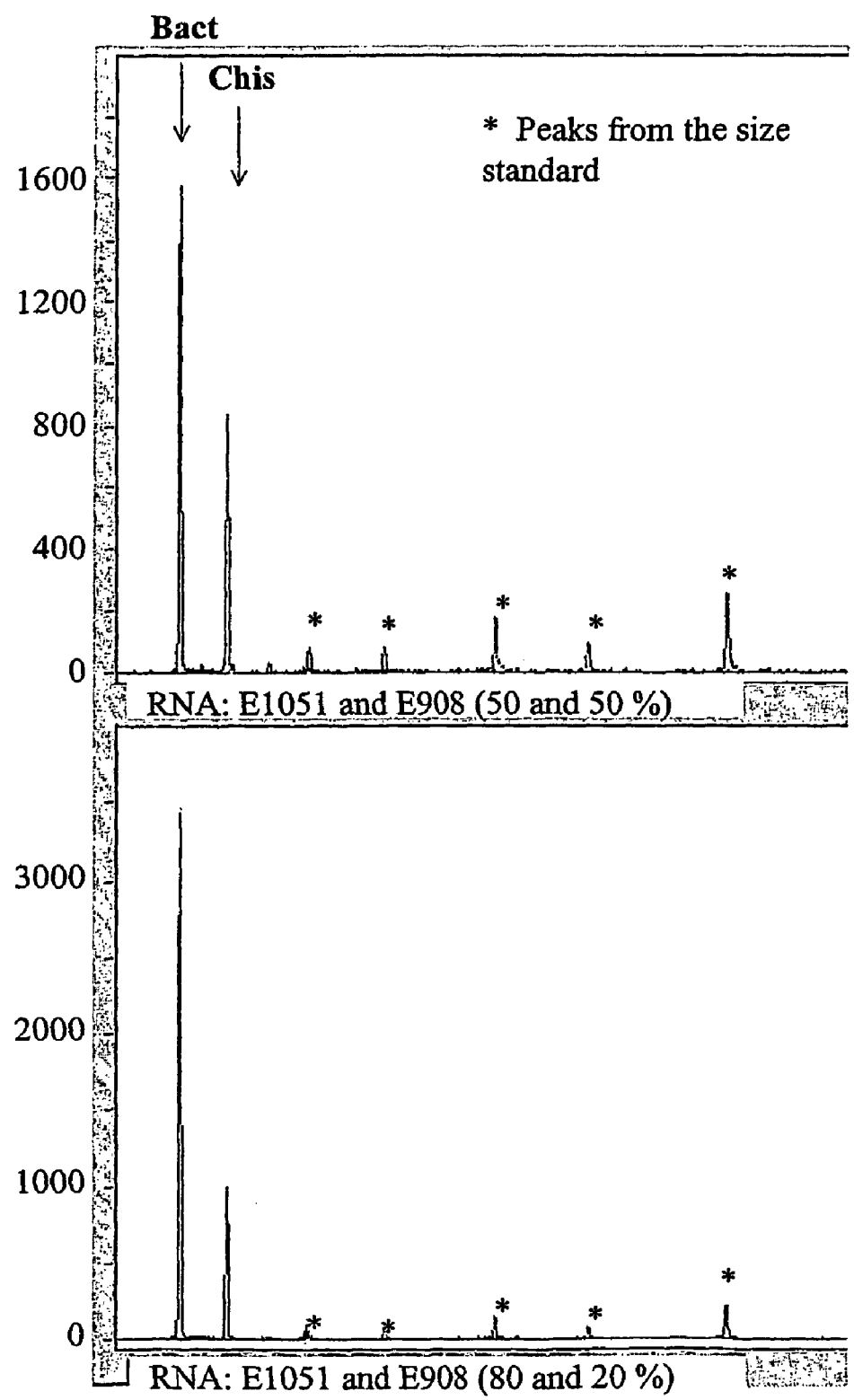

FIG. 10B depicts results obtained when analysing a microbial population comprising *C. tyrobutyricum* E908 and *C. symbiosum* E1051 with the probes Bact and Chis. The Bact probe identifies both strains, whereas the Chis probe identifies only strain E908. The proportion of RNA from each strain is given as percentage of the total RNA used for the hybridization.

FIG. 11 shows a semi-automated performance of the process as a flow sheet.

Figure 12:
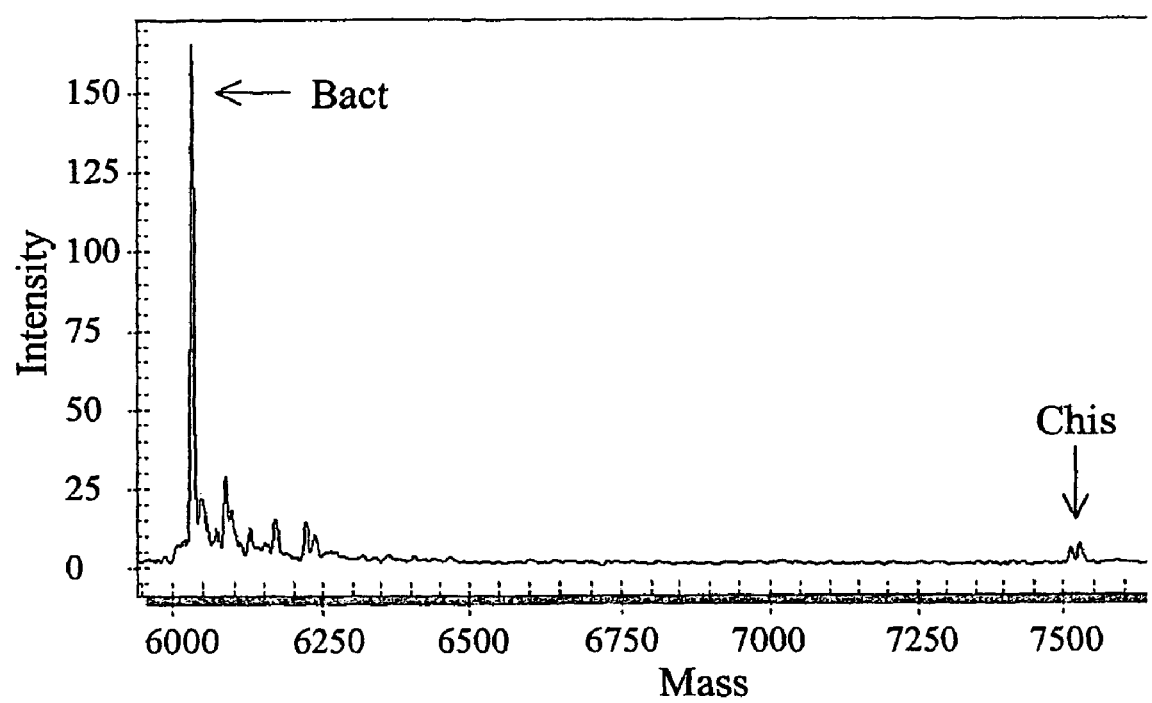

FIG. 12 shows the results, which may be recorded from a mass spectrogram and from a data file obtained when carrying out the qualitative and quantitative process of the invention according to Example 5. The signal intensities of the Bact and Chis probes correspond to their concentrations in the sample.

Figure 13:
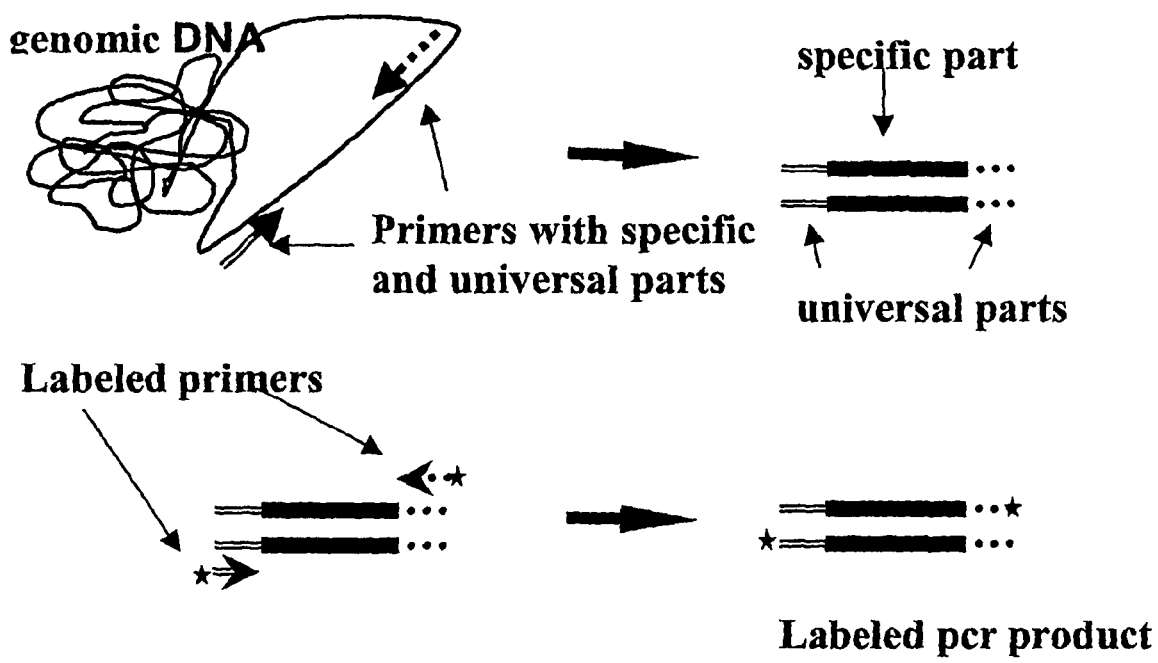

FIG. 13 is a schematic depiction of the preparation of the probes by PCR.

Figure 14:
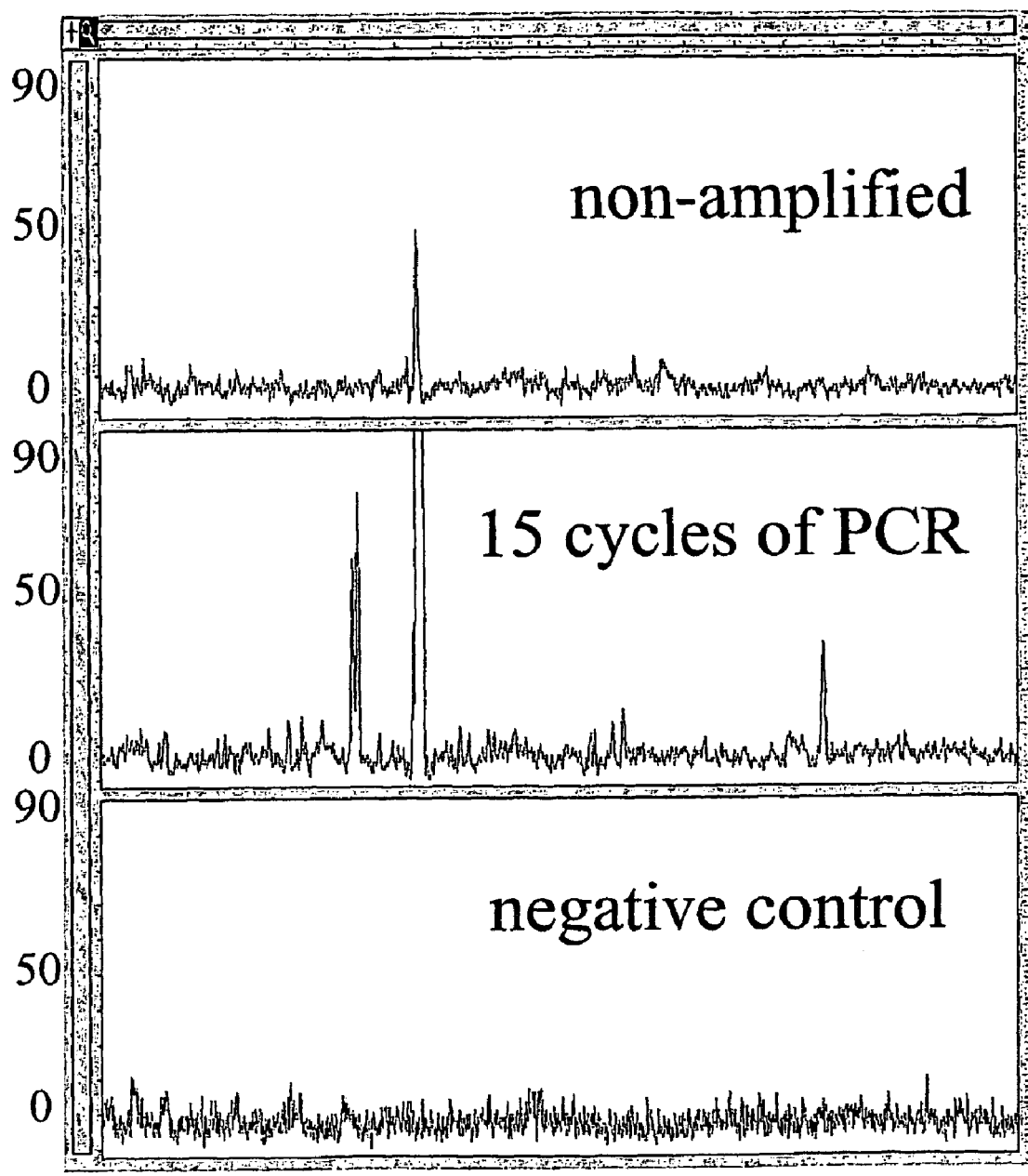

FIG. 14 shows electropherograms depicting the areas (fluorescence units) of probes from assays with the same amount of mRNA without (=non amplified) and with PCR-amplification (=15 cycles of PCR) and a negative control. Samples were run on an ABI 310 genetic analyzer.

DETAILED DESCRIPTION OF THE INVENTION

The terms used in the present invention have the meaning they usually have in the fields of recombinant DNA technology and nucleic acid hybridization technology. Some terms in the present invention are, however, used in a broader or somewhat different manner. Therefore, some of the terms are defined in more detail below.

Definitions

The term "target population" means a mixture of several varying individual organisms present in a sample comprising different more or less related individual organisms, which may be organized in groups or subpopulations, for example, according to their phylogenetic relationship. Examples of such mixed target populations are found in all crude samples that contain or have contained any living or dead organisms, including bacteria, fungi yeasts, plants and animals, etc. Environmental studies may be made e.g. from polluted soil samples. Bacterial populations inhabiting the intestines may be the focus of interest for hygienists. The amounts or relative proportions of *Salmonella, Shigella* and *E. coli* in a sample indicate the hygienic standards and possible health risks in food industry, restaurants and kitchens. Yeast populations may be checked for the presence of *Saccharomyces, Torulopsis, Candida*, etc. The information is important e.g. for excluding presence of contaminants. The amounts or relative proportions of *Aspergillus, Penicillium, Trichoderma* and other fungi may be used as an indication of fungal contamination in buildings. Another useful application of the method eventually providing rapid life saving results is the assessment of the effect of certain antibiotics on a sample from a patient suffering from a disease caused by antibiotic resistant bacteria.

Even plants and animals including human beings form populations, which may be grouped and tested by the method of the present invention.

The organisms may include any unicellular or multicellular organisms with characterized, partially characterized or uncharacterized genomes, which preferably include highly conserved, partially conserved or hypervariable regions, which allow the identification of the organisms and their organization in groups or subpopulations. The target population may originate from any specimens that contain or have contained living organisms, including microorganisms, plants, animals as well as human beings. The genomes of *E. coli, S. cerevisiae* and human beings represent organisms with genomes which at present are more or less fully characterized. The presence of polymorphism is a particularly interesting subject of the present invention.

In the present invention the population is assessed in the form of a polynucleotide mixture isolated from a sample comprising said population. The sample polynucleotide mixture comprises individual polynucleotide sequences and groups thereof, which may be identified with common, more or less conserved probes. The population may be divided in subpopulations, which represent different phylogenetic levels, including groups, genera, species or subspecies. By assessing the amounts or relative proportions of said individual polynucleotide sequences and subgroups thereof, it is possible to evaluate dynamic variation in the amounts and/or relative proportions of organisms or individual polynucleotide sequences taking place in a mixture of polynucleotide sequences or in a target population by taking sequential samples or by comparing samples from different sites or places.

It is to be noted that the polynucleotide sequences in the sample, i.e. the analytes, may be of any size. Generally, they are more or less fragmented polynucleotide sequences. In the present invention the reagents or probes used for identification are polynucleotide sequences, which have approximately the same number of nucleotides. The polynucleotide probes are rendered distinct with distinguishable sizes by providing them with resolution enabling tags, which are, for example, polynucleotide sequences, which may act as affinity tags, primer tags or simply as resolution enabling tracer tags. In the present invention oligonucleotides comprise from 2-12 base pairs, whereas probes having more than 15, e.g. 18-35 base pairs are prefered. Especially in more sensitive embodiments of the method of the present invention, in which PCR-amplification is used, the probes should have more base pairs, preferably at least 30 base pairs. Therefore, the probes of the present invention are defined as polynucleotide sequences. Principally, there is no upper limit, but it is self-evident that short probes are more cost effective and easier to prepare and handle. Long probes are also more difficult to make distinguishable by adding short resolution enabling tags. Therefore, the particular problem, which is solved by the characteristic feature of the present invention is not the length of the polynucleotide probes but how to get polynucleotides sequence having approximately the same number of nucleotides sufficiently distinguishable to enable accurate recording of the results.

The term "pool" means a mixture, subset or a library of soluble or solubilizable polynucleotide probes, i.e. relatively short polynucleotides having approximately the same number of nucleotides, i.e. the same size, which are complementary to and thereby capable of identifying the desired target polynucleotide sequences in the sample. Each pool comprises an optional defined number of polynucleotide probes. A convenient optional number is, for example, approximately 10 probes. However, the method may be used with as few as two or three probes, but a more convenient number of probes is five or more probes in each pool. Test kits with pools comprising hundreds of soluble probes may be prepared and used in the quantitative and/or comparative method of the present invention. Even if it is possible to prepare pools comprising thousands of probes, a prefered upper limit seems to be approximately 300-500 different probes in order to obtain a satisfactory resolution when recording the results. In other words, it must be possible to distinguish the probes from each others by mass spectrometry, chromatography or electrophoretic techniques. The pools are said to be "organized" because the contents of each pool are known and are placed in an organized, defined and recognizable manner in their own vessels, which may be marked and named to allow their identification. For example when series of pools are prepared on identical microwell plates, each well is characterized not only by its content but also by its place. Thereby, identification is accurately enabled.

In the present invention the "pools of polynucleotide probes" means a set or mixture of soluble polynucleotide sequences, i.e. DNA fragments, which are made from selected polynucleotide probes, capable of identifying the desired groups of organisms having an polynucleotide sequence, in common, e.g. conserved motifs. Such common polynucleotide sequences are well known and comprise more or less conserved regions, which may be found, especially in ribosomal RNA (rRNA), etc., but they are also present in other tissues and organelles containing polynucleotide sequences.

Ribosomes are present in all living cells and are known to comprise proteins and ribosomal RNA (rRNA). Said rRNA in turn comprises alternating conserved and variable regions with nine variable regions found, for example, in the bacterial 16S rRNA (FIG. 5). The rRNA genes (rDNA) are organized in rrn operons, where rDNA genes are separated by hypervariable spacer regions. Most organisms carry several rrn operons in their genome and in most cases the intragenomic sequences of the structural rRNA are highly similar. Analysis of rDNA sequences data, especially that of a small subunit rDNA has revealed variable regions in the gene sequences that contain information specific for different phylogenetic levels; groups, genera, species or subspecies (FIG. 6). Thus, sequences unique to certain organisms may be found. This has been utilized to design species and group-specific nucleic acid probes for detection and identification of bacteria and other microorganisms. Such more or less conserved regions or motifs that are more or less common for a multitude of other organisms, enable the individual organisms in a target population to be organized in certain groups or subpopulations. Therefore, the identification and comparative assessment of variations of individual organisms and subgroups in the target population is also enabled. DNA and RNA from other sources also comprise more or less variable or conserved regions, which may be used for specific identification of individual organisms or certain subgroups in target populations. Polynucleotide probes for other genes and the corresponding messenger RNA (mRNA) may be used to monitor functional properties such as antibiotic resistance in bacteria and gene allele polymorphism.

The term "surplus" means that the polynucleotide probes are present in a molar excess as compared to the analyte polynucleotides in the sample in order to achieve an accurate recording, which is a prerequisite for the quantitative determination. For accurate recording, the soluble polynucleotide probes must be present in a molar excess or surplus and they must be distinguishable, e.g. by mass.

In the present invention the "distinguishability" is achieved by providing the probes with so called "resolution enabling tags". The polynucleotide probes of the present invention, which enable identification of related groups of organisms and which are especially useful in the application of the present invention, generally, have approximately the same number of nucleotides. Before use, said polynucleotide sequences may be modified and provided with features, which make them distinguishable in a size-based separation, fractionation or recording system. This may be achieved by end-tailing the polynucleotide sequences with "resolution enabling tags", which change the mass of the probes and thereby provide them with different mobilities in the fractionation, separation or recording systems used. Preferably, the resolution enabling tags should simultaneously function as affinity, tracer or primer tags. Preferably, said tags should have more than one of the desired functions.

For example, the polynucleotide probes, which are present in excess as compared to the target polynucleotides, which are quantified, may be provided with polynucleotide sequences, including polyA, polyT, polyU, polyC, polyG, mixed polynucleotides, e.g. polyATs, polyGCs or other nucleotide combinations or other oligonucleotide sequences including any mixtures thereof. In addition to being resolution enabling tags, these oligonucleotide sequences may act as affinity tags and primer tags. Tracer tags or labels, e.g. fluorophores of different sizes not only enable detection, they are also useful as resolution enabling tags, if they have sufficient differences in size or mass. Amino acids or peptides, which do not disturb the hybridization reaction may be used as resolution enabling tags, but they may also function as affinity tags and tracer tags. There are several strategies reported for the synthesis of peptide oligonucleotide conjugates, which all are readily adaptable for the present invention. In order not to disturb the hybridization, it is recommendable to attach the resolution enabling tag only to one end of the probe. However, when primers are used as tags, they are naturally situated on both sides of the probe "Tracer tag", means a label or marker, which enables the detection and/or recording of the probe. In the basic embodiment of the present invention the tracer tag is a detectable or recordable marker or label such as a fluorophore. It is to be noted that the tracer tag is preferably placed in one end of the probe. The probe is end-tagged in order to prevent the tracer from disturbing the hybridization reactions between the probe and the analyte. In the present invention the tracer tag may also function as the resolution enabling tag by providing the probes with different masses and thereby different mobilities.

The term "tracer tags" means labels or markers, which are visible or otherwise detectable, i.e. directly recordable or which may be made detectable or recordable when contacted with other reagents. Tracer tags, recordable by their electrochemical or magnetic, including mass spectrometric properties, fluorescence, luminescence, infrared absorption, radioactivity or by enzymatic reactions, are especially appropriate. However, it is evident that any other tracer tags not mentioned herein, which tags are easily recordable by automatic means or instruments may be used. It is to be noted that no tracer tag is needed when mass spectrometry or chromatographic techniques are used for recording, but the polynucleotide probes having the same number of nucleotides have to be provided with other groups enabling resolution by size or mass.

Fluorescent dyes such as 2-((iodoacetyl)amino)ethyl)aminonapthylene-1-sulfonic acid) (1,5-IEDANS), fluorescein, Bodipy, FTC, Texas Red, phycoerythrin, rhodamines, carboxytetramethylrhodamine, DAPI, indopyras dyes, Cascade Blue, Oregon Green, eosins, erythrosin, pyridyloxazoles, benzoxadiazoles, aminonapthalenes, pyrenes, maleimides, coumarins, Lucifer Yellow, Propidium iodide, porhyrins, CY3, CY5, CY9, lanthanides, cryptates, lanthanide chelates, or derivatives or analogues of said tracer molecules are examples of suitable tracer tags. The fluorescent polynucleotide probes are especially useful in automatic or semiautomatic recording of the results combined with continuous flow systems and instruments. Fluorophores with sizes and masses differing to such a degree that they make the polynucleotide probes distinguishable may be found among those mentioned above. Especially, phosphoramidites such as 6-FAM™, VIC™, NED™, ROX™ and PET™ (all trademarked by Applied Biosystems) may be used to end label polynucleotide probes.

In certain embodiments of the present invention very small quantities of the analyte nucleotide has to be identified and a more sensitive test is required. In such cases the probe is provided with a pair of terminal primer sequences or "primer tags", which allow the amplification of the quantitatively recovered probes. Also in this case the probes may further be provided with optional tracer tags, e.g. with fluorophores of different sizes, especially during a PCR-amplification process. These primer tags placed in the 3'- and 5'-terminal ends of the probe allow amplification of the probes after a quantitative recovery of the probes hybridizing with the affinity tagged analytes. One of the primer sequences may be quite short, whereas the other may be longer and simultaneously act as an affinity tag and a resolution enabling tag. In this embodiment the probes may be provided with an optional tracer tag during or after the amplification. If mass spectrometry is used for recording, no tracers are needed. It is sufficient that the individual probes are provided with tags, which enable resolution, e.g. oligonucleotides acting as primers or affinity tags.

Amino acids and peptides, which do not disturb the hybridization reaction may be attached, preferably end-tagged to the polynucleotide probes. There are several strategies reported for the synthesis of peptide oligonucleotide conjugates, which all may readily be adapted for the present application. (See e.g. Lönnberg, H. Annu. Rep. Prog. Chem., Sect B 1999, 95, 207-234 and 2001, 97, 177-208). Similar chemical methods for preparing probes of different sizes may be used to link also other organic chemical residues than peptides to the polynucleotides. Said amino acid or peptide sequences may simultaneously act as "affinity tags" and/or "tracer tags". The amino acid histidine is a useful example. Peptides, including ligands may be used as "affinity tags". Peptides with enzymatic activities may act as "tracer tags". Peptides functioning as antibody-antigen pairs may act as affinity and tracer as well as resolution enabling tags.

The term "analytes" means the polynucleotide sequences, which are obtained from a sample comprising the target population. The mixture of polynucleotide sequences from the target population may include any nucleotide sequences, (DNA or RNA), including messenger RNA (mRNA), transfer RNA (tRNA), but ribosomal RNA (rRNA) or genes encoding such are especially useful. The target population may be sampled at different sites or places, and at different points of time, e.g. before and after a treatment, which should have an effect on the target population. The polynucleotide sequences in the sample of the target population are isolated by per se known methods, e.g. (Sambrook, J. and Russel, D., Molecular cloning—A Laboratory Manual, Third Edition (2001)). The sample preparation comprising the analyte polynucleotide sequences may be modified to include a suitable affinity tag.

The analyte polynucleotides may be affinity tagged by a chemical reaction, in which e.g. biotin residues are covalently linked to the polynucleotides or nucleic acid molecules to be studied resulting in modified polynucleotide analytes, i.e. a biotinylated polynucleotide analytes. In order to avoid that steric hindrances disturb the hybridization reaction between the tracer tagged probes and the polynucleotide analytes, the polynucleotide analytes are tagged with a smaller counterpart of an affinity pair, whereas its bigger counterpart is attached to a solid support or separation aiding tool. For analysing the composition of populations as represented by polynucleotide sequences, the affinity-tagged analyte polynucleotide sequences may be polynucleotide sequences of any kind, including total RNA or rRNA or gene preparations. The affinity tag and its counterpart or pair provides a so called affinity-pair, which allows the capture of affinity tagged substances to a solid support, which in this case is called a separation aiding tool.

"Affinity aided solution hybridization" is a well known method, wherein the hybridization reaction between a probe and an analyte nucleotide sequence is allowed to take place without any steric hindrances in a solution. The affinity tag allows the hybrids to be captured on a solid phase, which allows the separation and washing of the collected nucleic acids and thereafter the captured hybrids or probes may be released and measured.

"Affinity tags" applicable also as resolution enabling tags are found among oligonucleotide residues, amino acid residues such as histidine, peptides or sugar residues and also include haptens such as biotin. Some of these tags may also function as tracer tags. For example, labeled or unlabeled oligonucleotide residues may be used as affinity tags, primer tags and resolution enabling tags.

The term "affinity tags" means that the analyte polynucleotides are provided with a label or marker, which has a high affinity to another substance. In other words, the affinity tag is prone to form a strong bond with its counterpart or affinity pair. The strong bonds formed between affinity pairs enable the affinity-pair to act as means for capturing desired substances. A useful affinity pair is, for example biotin-avidin or biotin-streptavidin, but other synthetic or non-synthetic "affinity pairs" or binding substances may also be applied. Suitable "affinity pairs" may be found among receptors and ligands, antigens and antibodies as well as among fragments thereof. The prefered "affinity tags" of the present invention include smaller molecules such as biotin, histidine oligonucleotides, haptens, glycans, etc., whereas the prefered counterparts of the "affinity tags" include bigger molecules such as avidin, streptavidin, metal chelates, antibodies, lectins, etc. are used to cover the "separation aiding tool". In the present invention especially prefered affinity tags are polynucleotides, such as poly(dA), poly(dT), poly(dG), poly (dC) and mixtures thereof. In addition to being affinity tags they provide resolution enabling tags of different sizes.

The term "separation aiding tool" means preferentially solid supports, such as micro-beads, latex particles, magnetic particles, threads, pegs, sticks, microwells, affinity columns, which are provided with or covered with the counterpart or affinity pair of the "affinity tag". Optionally, the separation aiding tool may include e.g. phase separation or electrophoretic means, which are dependent on the presence of the counterpart of the affinity tag.

The pools of "soluble polynucleotide probes" are preferably prepared from a more or less characterized library of polynucleotide sequences using different methods including isolation from nature, synthetic methods, PCR-techniques or recombinant DNA techniques or combinations thereof (Sambrook, J. and Russel, D., Molecular cloning-A Laboratory Manual, Third Edition (2001)). The different polynucleotide probes capable of demonstrating a specific subgroup or individual, are arranged or placed in pools so that all polynucleotide probe molecules that represent a certain subpopulation have a distinct or characteristic size or mass, which enable their identification when using chromatography, gel electrophoresis or mass spectrometry.

Even if the use of characterized probes are prefered it is possible to prepare probe pools for poorly characterized genomes in the same manner as described in WO 02/055734 and thereafter provide these polynucleotide probes with resolution enabling tags defined above allowing their separation and recording.

The term "modified polynucleotide sequences" means that the set of synthetically prepared polynucleotide probes may conveniently be modified, e.g. the sugar phosphate backbone of the nucleotide sequences may be replaced by peptide bonds or made of so called locked nucleoside analogs. Modified polynucleotides are, for example, peptide nucleic acids (PNAs) described e.g. in WO 96/20212 or locked nucleic acids (LNA), described e.g. in WO 99/14226. Said modified polynucleotide probes may conveniently be applied in the method and test kits of the present invention. They may be copied using genomic DNA or cDNA as models. Often, they have improved properties, including improved stability and they may also have the advantage of being more easy to provide with tracer tags than unmodified DNA probes.

The "soluble organized pool" comprising "soluble or solubilizable polynucleotide probes" may be contained in any kind of vessels, which may be totally separate or connected either in a non-fixed or a rigidly fixed manner. In its simplest form, an organized pool comprises one or more vessels, for example test tubes or bottles, which may be connected together in a non-fixed manner for example in a rack for test tubes. A practical example of organized pools placed in vessels, which are connected together in a rigidly fixed manner is provided by the compartments or wells in or on a microtiter plate. As said above the soluble pools are preferably placed in an organized manner, e.g. in the wells on the microtiter plate. The soluble pools are organized in such a way that each pool and each polynucleotide probe in said pool is distinctly identifiable. Microtiter plates with their wells are typical, commercially available embodiments allowing organization and simultaneous handling of many organized pools. Naturally, other tailor-made more convenient organized pools with multiple compartments may be developed and constructed and provided with appropriate marks and instructions for use.

The results are recorded by optional automatic or semi-automatic means or instruments, including chromatographic techniques as well as mass spectrometry. The whole system may be fully or partly automized. The techniques for distinguishing the probes include separation or fractionation in sieving or non-sieving media with or without electrophoresis. Sieving media, include chromatographic separation in a matrix, such as a gel, which separates the probes based on the size or mass. Electric charges are not essential for the separation even if they may increase the mobility rate of the probes. In a non-sieving medium in which there is no matrix, which sieves the matter to be fractionated, probes with a constant ratio between mass and charge all move independently of size with the same rate. In polynucleotide sequences the addition of oligonucleotides does not change this mass to charge ratio. Therefore, in order to achieve different mobilities in non-sieving media, the probes have to be provided with non-charged substances which enable them to move with different rates. This difference in mobility is not achieved by adding primer tags or affinity tags consisting of nucleotide sequences of different sizes or by adding substances that do not change the mass to charge ratio in comparison to the normal ratio in nucleotide sequences.

Therefore, the methods for fractionating and separating the quantitatively recovered probes in the present invention should be adapted in view of the above discussed factors. The prefered methods for distinguishing the probes of the present invention is therefore mass spectrometry or chromatographic separation in sieving media. If separation is achieved by capillary electrophoresis the prefered mode is using a sieving medium which retards the mobility of probes with larger moleuclar mass. Conventional gel electrophoresis in e.g. polyacrylamide is also a prefered method. The essential feature of the organized pool of probes is that all the probes in a single pool may be separated and quantified by the fractionation method chosen, the principle by which fractionation is achieved is not essential.

The General Description of the Invention

The present invention is related to a method, which allows simultaneous, quantitative determination of the amounts or relative proportions of more than one individual polynucleotide or subgroups thereof in mixture of polynucleotide sequences using polynucleotide probes having approximately the same size. In one embodiment of the present invention the polynucleotide sequence represent selected individual organisms, subgroups, genera, species or strains, which are present in a sample representing a target population of more or less related organisms. Variations in the amounts of subgroups or individual organisms in the population due to inherent causes, such as aging or external stimuli, such as antibiotic treatment, hygienic measures, may be assessed. In another embodiment of the invention variations in the amounts or relative proportions of transcripts of polynucleotide sequences in a single organism may be determined. This allows, for example, the demonstration of differences in the expression of non-homologous, allelic genes in a chromosome and may explain the reasons for different manifestation of certain diseases. It also enables the studies of polymorphism in one organism. The method and test kit are applicable for environmental and population studies. In the basic principles of the method of the present invention comprises a hybridization reaction that is allowed to take place in a solution and the hybrid formed is collected or captured on a solid support provided or covered with the counterpart or affinity pair of an affinity tag. The covering is achieved by chemical means, e.g. by conjugation. Sometimes the affinity between the surface(s) of the solid separation aiding tool and the counterpart of the affinity tag is sufficient to form a stable binding. Tracer-tagged, preferably end-tagged polynucleotide probes from a previously characterized, partially characterized or uncharacterized pool (library) are contacted with the affinity-tagged analyte polynucleotide sequences obtained from the sample to be analyzed.

One or more soluble pools are provided with preset, but optional numbers, preferably varying between 2-500, more preferably between 5-400, most preferably between 10-300 soluble polynucleotide sequences. A prerequisite for the method is that the polynucleotide probes, which are of approximately the same size, are made distinguishable by attaching or end-tailing the polynucleotide probes with "resolution enabling tags" which allow their separation or fractionation and enables resolution of the individual polynucleotide probes in such a manner that an accurate identification and calculation of results may be obtained, e.g. by electrophoretic techniques, mass spectrometry or chromatography.

The soluble polynucleotide probes may be identified without any tracer tags using e.g. mass spectrometry. Alternatively, they may be provided with tracer tags, which in the basic embodiment of the present invention are directly detectable or recordable labels and markers which simultaneously may act as resolution enabling tags. In a more advanced embodiment of the invention allowing an ultrasensitive detection or comparative assessment, it is preferable to use polynucleotide probes and not too short oligonucleotides and to provide said polynucleotide probes with a pair of terminal primer tags, which enable a polymerase chain reaction (PCR) to take place after the quantitative recovery of probes. During the amplification the probes may be provided with tracer tags using e.g. tracer tagged primers or labeled nucleotides. In this case the resolution enabling tag must not be a tracer tag. The soluble pools are placed in an organized manner in their own vessels, which may be separate, loosely connected or removable. The organized pools may also be placed in or on a more compact structure, wherein the vessels are more or less rigidly joined together as the wells on a microtiter plate.

In the basic embodiment of the present invention resolution enabling tags, providing the polynucleotide probes with differences in the size or mass to electric charge ratio are allowed to hybridize with or without tracer or primer tags with the analyte polynucleotide preparation obtained by isolating from the sample containing the target population. The analyte polynucleotide sequences, present in the sampled target population are isolated by per se known methods. Generally, the analyte polynucleotides to be determined from target population are ribosomal RNA (rRNA), messenger RNAs (mRNA) or their corresponding genes (DNA). Said analytes are provided with at least one affinity tag, such as biotin, histidine, oligonucleotide sequences, such as oligo(dT), -(dA), -(dC), -(dG) or mixtures thereof, as well as haptens or glycans. The analyte polynucleotides are preferably labeled with biotin.

After these reagent preparation steps, the hybridization reaction between the probes and the analytes is allowed to take place. Hybrids are formed in a molecularly accurate quantitative manner between the soluble polynucleotide probes and the affinity tagged analytes. Because the different polynucleotide probes present in the pools are known and because there is an excess of each probe as compared to the analytes, it is evident that the hybridization reaction between the analytes and the probes, which results in a hybrid is stochiometrical and the amount of probe recovered corresponds to the amount of analyte polynucleotides present in the sample. Naturally, the analyte sequence need not be a rRNA sequence. It is possible by the present method to quantitate any single stranded sequence as well as any double stranded sequence, after a denaturation step rendering the double stranded analyte single stranded.

As described above by the hybridization in solution DNA:RNA (DNA:DNA) hybrids will form. Generally, the solution hybridization is performed in conditions, which drive the hybridization towards the formation of hybrids, including DNA:DNA, DNA:RNA, RNA:RNA, PNA:DNA, PNA:RNA, LNA:DNA, LNA:RNA, etc. The most prefered conditions vary depending upon the polynucleotide probes, analytes, etc. Thereafter, the hybrids, by the aid of the analyte polynucleotide sequences carrying the affinity tag due to their affinity to their counterpart are collected or captured on the separation aiding tool covered by said counterpart of the affinity tag. Only such polynucleotide probes, which have been able to hybridize with analyte sequences are collected on the separation aiding tool and may be quantitatively recovered, optionally amplified and recorded. The captured and collected hybrids are removed or separated from the hybridization solution and may be washed free from other reagents and unreacted probes. The polynucleotide probes, which have not formed hybrids with the affinity-tagged polynucleotide analytes will remain in the hybridization or wash solutions and accordingly they are removed. The captured and collected hybrids may be washed free from excess probes, including such probes which have not been able to hybridize with an affinity tagged analyte sequence. In such cases, an analyte sequence representing a certain individual organism or subgroup in the target population and corresponding to the polynucleotide probe has not been present in the sample. The collected polynucleotide probes, which may be separated or released from the analyte are optionally provided with a tracer tag. In this case the resolution enabling tag must not be a tracer tag. Redundant affinity tags and affinity tagged analyte sequences, which have not been able to hybridize, because no corresponding probes have been present in the pool are naturally captured on the solid separation aiding tool, but may be separated from the hybrids during the elution and subsequent separation processes. Also such affinity tagged analytes, which do not have a complementary strand among the probes are captured on the separation aiding tool, but they do not disturb the stochiometry of the hybridization process and they do not disturb the consequent analytical steps. They may, for example, be destructed or removed when the probes are isolated or released from the hybrid and/or the separation aiding tool.

Separation aiding tools (SAT) are required in the method of the present invention in order to recover the hybrids formed between the optionally tracer tagged probes and the affinity tagged analytes. The separation aiding tools, which are solid supports, such as microparticles, microbeads, latex particles, magnetic particles, threads, pegs, sticks, microwells and affinity columns are provided or covered with the counterpart(s) or affinity pair(s) of the affinity tags. The separation aiding tool may comprise means for phase separation or electrophoretic means for capturing the counterpart of the affinity tag.

The hybrids recovered on the separation aiding tool are subsequently released from the tool first by eluting, and thereafter by breaking the hydrogen bonds of the hybrids and the optionally tagged individual probes which have been released from the hybrids are isolated, separated by their sizes and recorded with means allowing their quantification.

Because each probe represents an analyte polynucleotide sequence in the sample, the amounts or proportional ratios of individual polynucleotides sequences representing individual organisms may be quantitated on a molecular basis. Alternatively, the bonds of the hybrid are first broken and thereafter the solid support and the solution containing the probes are separated from each other by an appropriate method dependent on the separation aiding tool used. Thereafter, e.g. by centrifugation, the probes are separated based on their size and recorded by means allowing their quantification. The purified and isolated probes on the separation aiding tools are eluted with a solution, such as NaOH, $NH_4OH$ or formamide capable of breaking the bonds between the polynucleotide strands.

Consequently, only those polynucleotide probes, which have been able to hybridize to an analyte polynucleotide representing a certain individual organism or subgroup of organisms in the target population, i.e. only those polynucleotide probes, which have a complementary stranded analyte polynucleotide sequence present in the sample are captured by the separating aiding tool and may be recovered for recording.

This means that the automatically or semiautomatically detectable or recordable optionally tracer tagged probes, which are identifiable by their distinct sizes or may be made distinguishable, are captured or recovered and subsequently released or isolated for recording. It is evident for one skilled in the art that the order of performing the steps in certain case may be changed.

If the tracer tag is lacking, the probes may be directly recorded with mass spectrometry. If the tag is a tracer, e.g. a fluorescent substance, the probe may also be directly recorded, when it has been separated from the analyte polynucleotide, which does not have any tracer tag. The optionally tracer tagged reagent probes are now present in an isolated and free form and their amount corresponds exactly to the amount of analyte nucleic acid previously hybridized to them.

If the tag is a pair of terminal primers, optionally with a tracer tag, the probe may be amplified after separation from the analyte polynucleotide sequence and provided with a tracer tag, either during or after the amplification. For example, after an optional number of amplification cycles, the polynucleotide probes may be provided with a tracer tag and recorded. Alternatively, the complementary primers may be provided with tracer tags, thereby the probes are provided with tracer tags during the amplification. The amplification allows the recording of subpopulations or polynucleotide sequences present in such minimal amounts that it is under detection limit when other methods are used. In said advanced embodiment of the present invention, which allows a more sensitive assessment of the analyte polynucleotides, the tags on the probes are terminal primer sequences. The terminal primer tagged probes are allowed to hybridize with the affinity tagged analyte polynucleotides in the same way as in the basic embodiment of the present invention. After the stochiometric hybridization reaction, the hybrids are captured on a separation aiding tool and the primer tagged probes are recovered by per se known methods. The amount of recovered probes, which correspond to the amount of analyte polynucleotides present in the sample may be amplified an optional number of times by per se known PCR-techniques. Thereafter or during the PCR-amplification, the probes are optionally provided with tracers and the amount of the probes is recorded. Because the recovery of the primer tagged probe is quantitative and corresponds to the number of analyte molecules and it is known, with the aid of the include molecules of known amount, how many times the probes were amplified, i.e. multiplied or copied, it is easy to calculate the amount of analyte in the original sample. This allows a quantitative assessment even of such analyte polynucleotides, which without the amplification would have been under detection limit and thus not recordable. Accordingly, the sensitivity of the method of the present invention may be highly increased. This is a great advantage, if a very sensitive test is needed, for example when the sampled population, e.g. a biopsy sample, contains only a few organisms or cells.

Thus, the affinity selected probe profile may be assessed by sensitive automatic or partly automized, quantitative recording systems, after separating the probes from each other based on their size, e.g. by chromatographic, electrophoretic techniques, including capillary or gel electrophoresis as well as mass spectrometry. The polynucleotide probe, which is rendered recordable by providing it with a distinguishable size or mass and which is present in a specific pool, always corresponds to a complementary analyte molecule, which may be identified by the known probe. Hence, the individual polynucleotides in a mixture of polynucleotides or in a mixed target population may be very accurately deduced.

A comparative quantitative assessment of variations in the amount of various polynucleotides present in cell or tissue sample as a response to inherent changes due to inherent control mechanisms or as a response to external stimuli, including drugs, pathological states requires at least two organized soluble pools, but preferable at least one organized pool for each sample to be tested. Each pool comprise identical polynucleotide probes, but the organized pools, e.g. each in its own well on a microtiter plate, is optionally provided with a recordable tracer tag. If tracer tags are used it is advantageous to use distinguishable tracers, e.g. fluorophores having different wavelengths of emission. In a prefered embodiment the soluble pools are provided on microtiter plates. Each microtiter plate is otherwise identical, but each has its own specific recordable tracers, which if they are fluorophores preferably emit at different distinguishable wavelengths of emission, which allows simultaneous recording of the variations. It is possible to compare the amounts without tracer tags using mass spectrometry and allowing computer based automatic systems to calculate and compare the recorded results.

The following flow chart of the method describes how to carry out the present invention:

Preparative Steps

Step 1—Preparation of Organized Pools of Soluble Polynucleotide Probes Having Approximately the Same Sizes Case 1—Selecting Regions from Ribosomal RNA The rDNA fragments are selected to represent more or less conserved or variable regions representing a certain species or group of bacteria or microorganisms. The DNA fragments are provided with resolution enabling tags or tails or labels allowing a good resolution in the size fractionation-stage.

(a) polynucleotide tailing (See step 2)

(b) tracer labeling (See step 2)

(c) protein-tailing (See step 2)

Case 2—Selecting Regions from Other Sources

The polynucleotides are selected to represent regions of other genes e.g. antibiotic resistance genes or their corresponding mRNA. Polynucleotide sequences capable of distinguishing between different alleles of the same gene may also be selected.

Step 2—End-Labeling the DNA Probes with a Tracer, Fluorophores or Size Providing Tail Preferably, two (or more) sets of the DNA with distinguishable dyes are prepared. This allows simultaneous comparative studies of variations in polynucleotide amounts, particularly rRNA amounts due to shifts in populations or internal mechanisms, e.g. pathological stages or due to external stimuli, such as drugs. Steps 1 and 2 are preparative and the bases for the commercially valuable test kits. The DNA pools may be made in large quantities for a large number of experiments. Accordingly, there should not be any need to repeat this rather tedious phase frequently.

Analytical Steps

Step 1 Preparation of a Single Stranded Polynucleotide Analyte

Nucleic acid is isolated from the mixed population pool by per se known methods. The isolation of RNA from the cells is used during appropriate experimental conditions using per se known methods, e.g. (Sambrook, J. and Russel, D., Molecular cloning-A Laboratory Manual, Third Edition (2001)). If the polynucleotide analyte is double stranded the analyte has to be denaturated in order to provide the single stranded sequences required in the method of the present invention.

Step 2 Preparation of Affinity Tagged Analytes

The isolated DNA or RNA is affinity tagged, for example biotinylated using a chemical, nonenzymatic process. The photoactivated reagent photobiotin is convenient for this purpose and it is commercially available. As the RNA will not be transcribed to cDNA or otherwise enzymatically modified for labeling, the RNA may be prepared and kept in strong detergents such as SDS. RNAses are inhibited by SDS so it is easy to isolate intact RNA. However, fragmentation is not a problem, if not too heavy. The size of the RNA fragments will not affect the capturing capacity.

Step 3—Solution Hybridization

Contact each of the soluble tracer tagged probe (DNA) pools with an aliquot of the affinity tagged analyte (RNA) preparation. Allow the hybridization to take place in the free solution in the small volume provided in respective pool compartment. This gives a fast and quantitative reaction.

Step 4—Separation Step

Add microbeads or another separation aiding tool carrying the affinity pair, e.g. avidin to capture the RNA molecules. Wash to get rid of free DNA.

Step 5—Recovering Stage

Elute with a solution which breaks the DNA:RNA hybrid such as formamide or NaOH. If necessary, concentrate probes by evaporation of the elution solution or precipitate and wash the single-stranded DNA. Take up the single stranded DNA in an electrophoresis sample or buffer solution. It is preferable that such conditions are used that electrophoresis of the eluate may be carried out directly and the different probes recorded simultaneously.

Step 6—Recording of Results

Determine the size and amount of DNA eluted from DNA:DNA or DNA:RNA hybrids by chromatography or gel electrophoresis. Mass spectrometry may be used as well. Differences in two DNA/RNA preparations are easily observed by hybridizing to DNA fragments labeled with different dyes and mixing the DNAs prior to electrophoresis.

Step 7—Interpretation of the Results

In case 1, the composition of the population becomes directly determined in the respect of subpopulations for which probes were included in the pool. Likewise, in case 2 the presence of certain functional properties (presence or expression of genes) in an individual organism or a population becomes directly determined.

Step 8—Optional Amplification

If a very sensitive assay is needed the reagent polynucleotide sequences, i.e. the tracer-tagged probes eluted from the separation aiding tool may be amplified by PCR after the quantitative selection step. If this approach is used, the reagent polynucleotide sequences, i.e. the probes, should be modified to contain a common terminal sequence allowing amplification of all the probes in the same pool with the same PCR primer pair, provided with a tracer tag.

When the probes are provided with tags or tails allowing their separation by size or mobility by gel-electrophoresis or chromatography. They may also be recorded based on their masses using mass spectrometry. In this case, no tracer tags are required and further improvement of the method is enabled. By omitting the use of tracer tags, the method may be simplified and the need of expensive recordable labels may be avoided. Otherwise, the method fully corresponds to the method as described above and comprises the following consecutive steps:

(a) providing, one or more organized pools with a preset optional number of soluble probe polynucleotide sequences with distinct sizes allowing their identification or recording, said pools being placed in an organized manner in their own vessels which are separate or joined together;

(b) isolating the analyte polynucleotide sequences present in a cell or tissue sample of the target organism and providing said analytes with at least one affinity tag;

(c) allowing a hybridization reaction to take place between the soluble probes from the step (a) and the analyte from step (b) leading to formation of soluble probe:affinity tagged analyte-hybrids;

(d) isolating the probe:analyte-hybrids formed in step (c) by capturing said hybrid on a separation aiding tool provided with the affinity pair of the affinity tag of the analyte;

(e) recovering the probe from the separation aiding tool; and (f) recording the size and amount of probe with electrophoretic techniques or mass spectrometry.

Test Kits

The present invention is also related to a test kit for performing the quantitative determination. The test kit comprises one or more soluble organized pools with a preset optional number of soluble polynucleotide probes, which hybridize with complementary analyte nucleotide sequences, including more or less conserved or variable regions, which are common for the whole population or specific for a certain subgroup of organisms. Alternatively, the test kit comprises probes, which hybridize with specific genes encoding for certain functions and their corresponding mRNA such as those of antibiotic resistance. The polynucleotide probes are optionally provided with tags, either tracer tags or a pair of terminal primer tag sequences. Preferably, the tracer tags are end-labeled detectable tracer tags, such as fluorophores, providing different sizes to the polynucleotide probes.

The test kit comprises soluble organized pools, each pool having more than one, preferably more than ten, most preferably about hundred or more probes. The pools are preferably placed in an organized manner in their own vessels, e.g. test tubes, bottles or in the wells or compartments of a microtiter plate. Even if the test kit for performing the present quantitative determination preferably is a microtiter plate or a corresponding tailor-made structure, the test kit may be an optional number of test tubes, bottles, etc., which may be organized in more or less fixed arrangements, including racks and/or other rigid structures. The test kits may be customized or tailor-made and provided with appropriate marks and instructions for use.

The pools of soluble polynucleotide probes for the test kits may be prepared from fragments of DNA. They may be synthetic polynucleotides and modified DNAs. When the test kit is prepared for studying characterized genomes, the pools of the test kit preferably comprise at least one polynucleotide fragment (probe) from each gene to be studied in the genome. Also when uncharacterized genomes are to be studied, the pools may advantageously be prepared in larger quantities, commercial production is in no way excluded, for more general or more specific studies.

If the reagent polynucleotide probes are derived from a characterized genome each probe molecule is known to correspond to a given gene, and each probe is specifically identified by its size and pool. The variations of amounts or relative proportions of organisms or subgroups thereof in a certain mixed population may thus directly be compared and automatically calculated from the automatically recorded results. If the reagent polynucleotide probes are poorly characterized, they are for instance derived from an organism, the genome of which is not sequenced, valuable results may still be obtained.

A prefered embodiment of the test kit may be prepared on a microtiter plate. In such a practical embodiment of the invention, pools with DNA fragments from known or unknown sequences of yeast, clostridia, bacteria causing food poisoning, etc. may be used for preparing the test kits. If each pool comprises e.g. approximately 10-100 probes or fragments, it gives a sufficiently good resolution. If each probe in the pool represents a given bacterial species, probes for thousands of species may be placed on a single microtiter plate and there is still place for a number of controls. The captured DNA probes are identified partly by the pool or microtiter well to which it belongs, and partly by their size.

The optional recordable tracer tag is advantageously selected from a group of tracers detectable by fluorescence, infrared absorption, electromagnetic properties, radioactivity and enzymatic activity. The prefered tracer tag recordable by its fluorescence is a fluorochrome or a fluorophore. Mass spectrometry is another prefered mode, which allows recording and quantification without any tracer tags. Even if tracer tags are prefered embodiments they are not essential for the method of the present invention, the only prerequisite for the test kit of the present invention is that the probes in the soluble organized pools have distinct sizes or may be made distinguishable. They are optionally tagged, either with tracer tags or terminal primer tags. Accordingly, a working test kit is provided by an organized pool of terminal primer tagged probes even if no tracer is provided.

The test kit of the present invention in its simplest form is an organized pool of soluble tagged probes with distinct sizes. It is to be noted that said test kit is complete as such but may be complemented with optional tracers, affinity pairs and/or separation aiding tools. However, said auxiliary reagents are no prerequisite. Said auxiliary reagents and means for performing the method of the invention are available even commercially from several other sources. Thus, the method and test kit of the present invention may be tailor-made for the specific needs of the end-user, especially, they should be applicable for automatic or semiautomatic handling.

The mode of test kit manufacturing, which accordingly need not include immobilization steps, allows for easy adaptation of tailor-made tests, directing the attention to certain subsets or subpopulations of organisms in a given population. The test kit may comprise an optional affinity tag for labeling the polynucleotides in the cell or tissue sample and optional separation aiding tool provided or covered with a counterpart of the affinity tag for labeling the analyte. The optional affinity pairs providing the affinity tags for the analytes and the counterparts for the separation aiding tools include, but are not limited to, for example, biotin and avidin or streptavidin, histidine and metal chelates, haptens and antibodies or glycans and lectins.

The optional separation aiding tool, which may be incorporated into the test kit or may be provided separately, is selected from a group of solid supports consisting of microparticles, microbeads, latex particles, magnetic particles, threads, pegs, sticks, microwells or affinity columns. The separation aiding tool may include means for phase separation or electrophoretic means for capturing the counterpart of the affinity tag.

For the comparative assessment of variations of the amounts or relative proportions of individual polynucleotide sequences or subgroups thereof in a mixture of polynucleotide sequences, organized pools with identical sets of probes may be provided. In this case, each organized pool or test kit is optionally provided with optionally different or distinguishable tracer tags, which tags are distinguishable based on their sizes or mobilities and preferably emit at different emission lengths.

If the tags are terminal primer tags simultaneously acting as resolution enabling tags, the test kits are identical, but after the amplification the recovered and/or amplified probes may optionally be provided with distinguishable tracer tags. Alternatively, the complementary primer pair may be provided with a tracer tag, allowing tracer tagging during amplification. These auxiliary reagents may optionally be incorporated in the test kit or provided from other commercial or non-commercial sources. In order to enable simple comparative assessment of variations, in polynucleotide amounts in a sample, it is convenient to prepare test kits provided with different and distinguishable tracer tag emitting at different emission lengths and which may be recorded with automatic or semi-automatic instruments.

Test kits for comparative quantitative assessment of variations in the amounts of various individual polynucleotides or organisms or subgroups thereof in a mixture of polynucleotides or a target population as a response to inherent changes or external stimuli, including antibiotics, pathological states, epidemiologic conditions, conveniently comprise at least two solid supports or microtiter plates. Each solid support or microtiter plate is provided with identical pools of polynucleotide probes, optionally provided with the tracer tags. Each solid support or microtiter plate should optionally be provided with its own distinguishable tracer tag, which allows simultaneous recording of cell or tissue samples obtained at different times, for example, before or after drug treatment. Population profiling, i.e. analysing the differences in two or more analyte polynucleotide preparations, are easily recordable by hybridizing the analyte samples to reagent polynucleotide probes end-labeled with different, distinguishable and automatically recordable tracer tags.

After the hybridization step the different samples may optionally be mixed and their differences directly observed by measuring the ratio of the tracer tags to each other in each peak. The test kit may also be provided with at least one pair of primers for amplifying the tracer tagged probes obtained in the last step, for increasing the sensitivity of the test.

The method of the present invention is useful for quantitative and comparative assessment of variations in the amounts of certain organism and subgroups thereof in a sample of a selected mixed population.

The human gastrointestinal tract is probably the most complex microbial ecosystem described and it has been estimated that at least 400 bacterial species reside in the human large intestine. In order to study this extremely complex ecosystem convenient high-throughput analytical tools such as the described invention are needed. The present invention allows simultaneous screening of the presence of numerous bacterial groups and species and their relative quantitation in gastrointestinal samples. For example, in functional food studies a particular interest is to follow changes in the intestinal microbial populations. Bifidobacteria and lactobacilli belong to the indigenous microbial population of the human intestine and they are considered to be the marker organisms of well-balanced gut microbiota. Bifibacteria and lactobacteria often monitored in nutritional interventions. Genus- or group-specific probes as well as many species-specific probes are available for bifidobacteria and lactobacilli and thus, the described invention is readily adaptable for the detection of these bacteria. Another important group of intestinal bacteria are clostridia, some of which are potentially pathogenic. The enumeration of clostridia is troublesome due to inadequate selective media, but the described invention provides a culture-independent approach for qualitative and quantitative monitoring of clostridia as well as other microbial groups.

The described invention may also be utilized in clinical microbiology e.g. in assessing the efficacy of antibiotic treatment on bacterial populations. In order to find the correct antibiotic treatment in urgent situations with infections caused by antibiotic resistant bacteria rapid screening methods are especially valuable.

In drinking-water supply and food and feed production hygienic measures and good control are required. Based on the described invention test kits for controlling the microbiological quality of drinking water and food products may be designed. In food industry reliable tests for pathogenic microbes such as *Salmonella, Listeria, Bacillus* and *E. coli* take priority, but also tests for non-pathogenic food spoilage microbes such as lactobacilli and yeasts are often needed.

Another field of application for the invention are test kits for detecting fungi, which may grow in building structures and thereby cause serious health problems for humans by releasing toxins and spores to indoor air. Microbes may also cause damage to buildings and historically important artifacts such as ancient wall paintings, sculptures etc. Appropriate test kits may be designed for the identification of causative microbes are and monitoring the effectiveness of control measures.

In microbial ecology culture-independent monitoring methods are essential, because the laboratory growth conditions often fail to mimic the natural environments of microbes and consequently, only a fraction of microbes in environmental samples may be recovered on laboratory media. Different tests may be designed for monitoring uncultured microbial populations in different soil and water samples, which allow the evaluation of the effects of pollution, agriculture and other human actions on natural ecosystems and the efficacy of corrective measures environmental damages such as oil spillage. In fundamental ecological research the monitoring of natural seasonal variations in the microbial ecosystems and the comparison of similar ecosystems in different geographical locations is interesting.

Test kits may comprise of polynucleotide probes, which may discriminate between certain alleles of genes. Such kits may be used for population studies to study the distribution of certain alleles of genes, for example. Likewise polynucleotides, which recognize point mutations in various genes may be used in the kits.

In addition to the applications listed above, the method and test kits may be used for evolutionary studies and to evaluate relationships. In archeology, it may be used to study the causes of degradation of ancient wall paintings and statues and other artifacts by microbes and monitoring of the effect of preventive measures.

The method and test kits may be used for detection of point mutations with potentially detrimental effects on the health of humans and animals and for population studies including distribution of certain alleles of genes in the population The test kit of the present invention in its simplest and cheapest form is otherwise the same as the test kits described above and comprises one or more organized pools with a preset optional number of soluble polynucleotide sequence probes provided with distinct sizes allowing their identification and recording with mass spectrometry. The probes may be provided with terminal primer tags in order to allow amplification before the quantitative measurement with mass spectrographic or -spectrometric means. Said pools of unlabeled probes are placed in an organized manner in their own vessels, which are separate or joined together.

The test kit including the reagents of the present invention are preferably applicable for carrying out automatic or semi-automated processes, an example of which is shown as a flow sheet in FIG. 11. The process may be interrupted and the reagents transferred to other solid supports if the automatic devices are not quite compatible. The first steps are advantageously carried out in an automated pipetting station, wherein the biotinylated sample RNA is pipetted into each pool containing the distinctly sized probes in the pools. Thereafter, the test kit may be dried using a lyophilisator. The drying is made to eliminate the influence of any differences in volumes. The optional lyophilization allows the work to be stopped until it is convenient to continue the work.

The work may be recontinued by adding an appropriate hybridization buffer to the pools in an automated pipetting station. The plate is sealed with appropriate means, e.g. a film or a foil in order to avoid evaporation in the subsequent step. When the test kit has been provided with an appropriate heat-sealer, it is positioned into an automated thermal block, where the temperature may be up- or downregulated as required to enable the denaturation and hybridization of the probes. After hybridization the solution containing the probe:analyte-hybrids are placed in a magnetic particle processor in order to carry out the affinity capture, washing and elution steps by moving steptavidin/avidin coated magnetic beads from step to step e.g. on a KingFisher plate according to a programmed protocol. The eluates may optionally be transferred into a new plate, if the automated stations use different types of microtiter plates. The wells may be rinsed with elution buffer for quantitative transfer and then the combined solutions are evaporated in a lyophilisator, which enables preservation of the samples and making the recording at a more convenient time. In other words, the process may easily be adapted for different time schedules and protocols for performing the determination. The probe fragments, size standard and concentration standards are either directly or after a convenient step, automatically injected into an automatic analyser. The intensities of labels attached to the probe fragments are determined as peak heights or areas. The areas of the concentration standards, with known amounts, are then used to determine the absolute amounts each probe fragment.

The experimental design and the general principles of the present invention are described in more detail using bacterial strains available in the laboratory of the inventors and synthetic polynucleotides. The strains and polynucleotides are used for illustrative purposes only. The invention is in no way limited to said strains and polynucleotides or reaction solutions.

The principles of the invention may be checked by replacing the construct used in the examples by any other strains or polynucleotide sequences and probes, which are available in abundance. Those skilled in the art may easily adapt the principles of the invention in different applications.

EXAMPLE 1

Mobility of Probes in Electrical Field and Modification of Probes

Total RNA was extracted from *Clostridium symbiosum* strain VTT E-981051$^T$ (henceforward E1051) and hybridized with two 16S rRNA targeted probes Bact (Amann R. I., et al., Appl. Environ. Microbiol. 56:1919-1925, 1990) and Erec (Franks, A. H., et al., Appl. Environ. Microbiol. 64:3336-3345, 1998). Probe Bact is specific for bacteria (previously eubacteria) (Amann et al., 1990), whereas probe Erec is specific for bacteria belonging to the group of *Clostridium coccoides—Eubacterium rectale* (Franks, A. H., et al., Appl. Environ. Microbiol. 64:3336-3345, 1998). The species *Clostridium symbiosum* belongs to the *Clostridium coccoides—Eubacterium rectale*-group and thus its rRNA/rDNA was recognized by both probes Bact and Erec. In addition, Erec-5A—a modified version of the probe Erec with an attached 5A-tail (five additional adenosins)—was used in the model experiment. The experiment followed the steps set forth below:

Preparative Steps:

RNase free disposable microcentrifuge tubes, pipette tips, reagents, etc. were used in the preparative and analytical steps whenever necessary.

Step 1—Probes 16S rRNA targeted oligonucleotide probes

```
5' GCTGCCTCCCGTAGGAGT 3',        (SEQ ID NO:1)

5' GCTTCTTAGTCARGTACGG 3'        (SEQ ID NO:2)
and

5' GCTTCTTAGTCARGTACCGAAAAA 3',  (SEQ ID NO:3)
``` wherein R=A/G are listed in Table 1. and labeled with 6-FAM™ fluorophore in the 5'-end were purchased from Applied Biosystems:

TABLE 1

| | Probes | | |
|---|---|---|---|
| Probe name | Sequence | Length (nucleotides) | Reference |
| Bact | SEQ ID NO:1 | 18 | Amann et al., 1990 |
| Erec | SEQ ID NO:2 | 19 | Franks et al., 1998 |
| Erec-5A | SEQ ID NO:3 | 24 | buu |

Step 2—Preparation of Analyte

*Clostridium symbiosum* E1051 was grown as a pure culture in reinforced clostridial broth (Difco) in anaerobic conditions at 37° C. Total RNA from E1051 was extracted according to Zoetendal, E. G., et al., Appl. Environ. Microbiol. 64:38543859 (1998).

Analytical Steps:

Step 1—Affinity Tagging Analyte Sequences

RNA was affinity tagged with PHOROPROBE® Biotin SP-1000 according to the manufacturer's (VECTOR Laboratories) instructions. Subsequently, the biotinylated RNA was purified from free biotin with RNeasy mini kit by applying the protocol for RNA clean-up according to the manufacturer's (Qiagen) instructions.

Step 2—Solution Hybridization

An aliquot of the RNA sample (102 ng) was mixed with polynucleotide probe (1 pmol) in hybridization solution with final concentration of 5×SSC (0.75 M NaCl-75 mM sodium-citrate, pH 7.0), 0.1% (w/v) SDS and 1× Denhardt's (0.02% (w/v) Ficoll, 0.02% (w/v) polyvinylpyrrolidone, 0.02% (w/v) bovine serum albumin). The volume of the hybridization mixture was 20 µl. The reaction mixture was incubated at 70° C. for 2 min and then at 40° C. for 30 min.

Step 3—Affinity Capture, Washes and Elution

Following the hybridization, KingFisher magnetic particle processor (ThermoLabsystems) was used to perform affinity capture, washes and elution steps by moving streptavidin coated magnetic beads from step to step on a KingFisher microtiter plate according to a programmed protocol. Solutions for each step were pipetted beforehand to specified wells in the microtiter plates and the procedure was carried out in room temperature.

The hybridization reactions were transferred into specified wells in the KingFisher plate(s). In order to adjust the NaCl concentration suitable for the affinity capture (1M) and to transfer the hybridization mixture quantitatively into the KingFisher wells the hybridization tubes/wells were rinsed with 40 µl rinsing solution and the rinsing solution was subsequently added to the same KingFisher wells with the hybridization mixtures. The rinsing solution consist of one part of 2M NaCl-10 mM Tris-HCl (pH 7.5)-1 mM EDTA and 2.33 parts of hybridization solution (see Step 2).

Biotinylated RNA and RNA-oligonucleotide-hybrids were collected on streptavidin coated magnetic particles Dynabeads® M-280 (50 µg, Dynal A.S., Norway) for 30 min. Following capturing the particles were washed three times with 150 µl 1×SSC (0.15 M NaCl-15 mM sodium-citrate, pH 7.0)-0.1% SDS and twice with 150 µl of water (deionized, ultrafiltrated, RNase free) and the probes were eluted with 30 µl of formamide. Subsequently, the formamide was evaporated in a lyophilisator and the probes resuspended in 10 µl of water.

Step 4—Identification of Eluted Probes

The eluted probes were analysed by using ABI310 capillary electrophoresis equipment (Applied Biosystems). The eluted probes were identified based on their migration behaviour. Beforehand, free probes were run in the same equipment in same running conditions and their migration behaviour determined. In order to facilitate the comparison of individual runs (i.e. samples) size standard was added to the samples. The result was read from the electropherogram and from the data file as shown in FIG. 7.

As seen in FIG. 7 oligonucleotide probes differing in size only by one nucleotide were separated as individual peaks in capillary electrophoresis and the addition of 5A-tail to Erec probe significantly altered its migration behaviour. Despite the modification of probe Erec by the attachment of 5A-tail it recognized the target RNA from strain E1051.

EXAMPLE 2

Specificity of the Probes in a Protocol of the Invention

The specificity of two probes Chis and Erec (Franks, A. H., et al., Appl. Environ. Microbiol. 64:3336-3345, 1998) in the specified reaction conditions was ensured by hybridizing the probes with a number of bacterial strains. Probe Bact was used as an internal control in hybridization to ensure the integrity of bacterial rRNA. Chis is specific for bacteria belonging to the *Clostridium histolyticum* group (Franks, A. H., et al., Appl. Environ. Microbiol. 64:3336-3345, 1998). The probes Bact and Erec were previously described in Example 1. The experiment followed the steps set forth below:

Preparative steps:

Step 1—Probes

Chis 5' TTATGCGGTATTAATCTRCCTTT 3' (SEQ ID NO:4), wherein R=C/T; Franks, A. H., et al., Appl. Environ. Microbiol. 64:3336-3345, 1998) labeled with 6-FAM™ in the 5'-end was purchased from Applied Biosystems. The probes Bact and Erec were previously described in preparative step 1 in Example 1.

Step 2—Preparation of Analytes

Pure culture of different microorganisms form VTT Culture Collection (Table 2) were grown in adequate nutrient medium and total RNA from bacteria was extracted as described by Zoetendal, E. G., et al., Appl. Environ. Microbiol. 64:3854-3859 (1998) or with RNeasy mini kit by applying the protocol for the isolation of total RNA from bacteria according to the manufacturer's (Qiagen) instructions. Total RNA from *Trichoderma reesei* was extracted by using the TRIzol® Reagent method (Life Technologies; Gibco BRL).

TABLE 2

Test organisms

| | Strain Alternative Codes | | Target to probe | | |
|---|---|---|---|---|---|
| Species | VTT | International Culture Collection | Bact | Erec | Chis |
| *Clostridium acetobutylicum* | E-00022$^T$ | ATCC 824 | + | − | + |
| *Clostridium tyrobutyricum* | E-99908 | DSM663 | + | − | + |
| *Clostridium symbiosum* | E-981051$^T$ | ATCC 14940 | + | + | − |

TABLE 2-continued

Test organisms

| | Strain Alternative Codes | | Target to probe | | |
|---|---|---|---|---|---|
| Species | VTT | International Culture Collection | Bact | Erec | Chis |
| *Eubacterum rectale* | E-022088 | ATCC 33656 | + | + | − |
| *Clostridium leptum* | E-021850$^T$ | DSM 753$^T$ | + | − | − |
| *Clostridium lituseburense* | E-021853$^T$ | DSM 797$^T$ | + | − | − |
| *Trichoderma reesei* | D-74075 | ATCC 26921 | − | − | − |

Analytical Steps:

Step 1—Affinity Tagging Analyte Sequences

RNA was affinity tagged with biotin as described in analytical step 1 in Example 1. Following biotinylation, the biotinylated RNA was purified from free biotin according to the protocol provided by VECTOR Laboratories or with RNeasy mini kit by applying the protocol for RNA clean-up according to the manufacturer s (Qiagen) instructions.

Step 2—Solution Hybridization

An aliquot of the RNA sample (50 to 80 ng) was mixed with hybridization solution (see analytical step 2 in Example 1) containing oligonucleotide probes Bact and Chis or Bact and Erec (1 pmol each). The final volume of the hybridization mixture was 20 µl. The reaction mixture was incubated at 70° C. for 2 min and then at 50° C. for 30 min.

Step 3—Affinity Capture, Washes and Elution

Affinity capture, washes and elution were performed by using the KingFisher magnetic particle processor (ThermoLabsystems) as described in analytical step 1 in Example 1.

Step 4—Identification of Eluted Probes

The eluted probes were analysed by using ABI310 capillary electrophoresis equipment (Applied Biosystems) as described in analytical step 4 in Example 1.

As seen in FIG. 8 oligonucleotide probes Chis and Erec showed the expected specificity (Table 2) in the specified hybridization conditions and gave signal only with strains that belong to their target group. The probes showed expected specificity also with strains E-00022$^T$ and E-022088 which are not included in FIG. 8. Further, probe Bact also showed desired specificity and did not produce a signal with *Trichoderma reesei* RNA. RNA from strain E-021850 was partially degraded but still gave a signal with probe Bact showing that the method can be used also to analyse RNA that has been shared for example during the preparative steps. The specified hybridization conditions were the same with all three probes and hence, these probes can be used as a pool of probes.

EXAMPLE 3

Quantitative Evaluation

Total RNA was extracted from *Clostridium tyrobutyricum* VTT E-99908 (henceforward E908) and different amounts of RNA (0.01-10 ng) were hybridized with probes Bact and Chis. The experiment followed the steps set forth below:

Preparative Steps:

Step 1—Probes

Probes Bact and Chis previously described in preparative step 1 in example 1 and preparative step 1 in example 2 were used in the experiment.

Step 2—Preparation of Analytes

E908 was grown as a pure culture in reinforced clostridial broth (Difco) in anaerobic conditions at 37° C. and total RNA was extracted with RNeasy mini kit by applying the protocol for the isolation of total RNA from bacteria according to the manufacturer's (Qiagen) instructions.

Analytical Steps:

Step 1—Affinity Tagging Analyte Sequences

RNA was affinity tagged with biotin as described in analytical step 1 in Example 1. Following biotinylation, the biotinylated RNA was purified from free biotin according to the protocol provided by VECTOR Laboratories.

Step 2—Solution Hybridization

Total RNA extract from E908 was adequately diluted and an aliquot of the RNA sample (0.01; 0.05; 0.1; 0.5; 1.0 and 10.0 ng) was mixed with hybridization solution (see analytical step 2 in Example 1) containing oligonucleotide probes Bact and Chis (1 pmol each). The final volume of the hybridization mixture was 20 µl. The reaction mixture was incubated at 70° C. for 2 min and then at 50° C. for 30 min.

Step 3—Affinity Capture, Washes and Elution

Affinity capture, washes and elution were performed by using the KingFisher magnetic particle processor (Thermo-Labsystems) as described in analytical step 1 in Example 1.

Step 4—Identification of Eluted Probes

The eluted probes were analysed by using ABI310 capillary electrophoresis equipment (Applied Biosystems) as described in analytical step 4 in Example 1.

As seen in FIG. 9 the probe signal intensity (peak height and area) correlated well with the amount of RNA used in the hybridization. Both probes have target sites within 16S rRNA molecule but in different regions of the molecule. Probes Bact and Chis had equal level of fluorophore labeling and hence, the signal intensity from the probes were comparable.

EXAMPLE 4

Analysis of Microbial Populations

Total RNA was extracted from strains E1051, E908 and *Clostridium lituseburense* VTT E-021853 (henceforward E1853). Different amounts of RNA from these three strains were mixed and hybridized with a pool of probes consisting of probes Bact, Erec and Chis. The experiment followed the steps set forth below:

Preparative Steps:

Step 1—Probes

Probes Bact, Erec and Chis previously described in preparative step 1 in Example 1 and preparative step 1 in Example 2 were used in the experiment.

Step 2—Preparation of Analytes

Total RNA from pure cultures of E1051, E908 and E1853 was extracted as described in preparative step 2 in Example 2.

Analytical Steps:

Step 1—Affinity Tagging Analyte Sequences

RNA was affinity tagged with biotin as described in analytical step 1 in Example 1. Following biotinylation, the biotinylated RNA was purified from free biotin as described in analytical step 1 in Example 2.

Step 2—Solution Hybridization

Specified amounts of RNA from different bacteria (Table 3) were mixed and hybridization solution (see analytical step 2 in Example 1) containing oligonucleotide probes Bact, Chis and Erec (1 pmol each) was added. The final volume of the hybridization mixture was 20 µl. The reaction mixture was incubated at 70° C. for 2 min and then at 50° C. for 30 min.

TABLE 3

Hybridization experiments carried out in Example 4.

| Hybridization reaction | Probe pool | % RNA of total RNA | | |
|---|---|---|---|---|
| | | E1051 | E908 | E1853 |
| I | Bact, Erec, Chis | 100 | — | — |
| II | Bact, Erec, Chis | — | 100 | — |
| III | Bact, Erec, Chis | 20 | 20 | 60 |
| IV | Bact, Chis | 50 | 50 | — |
| V | Bact, Chis | 80 | 20 | — |

Step 3—Affinity Capture, Washes and Elution

Affinity capture, washes and elution were performed by using the KingFisher magnetic particle processor (Thermo-Labsystems) as described in analytical step 1 in Example 1.

Step 4—Identification of Eluted Probes

The eluted probes were analysed by using ABI310 capillary electrophoresis equipment (Applied Biosystems) as described in analytical step 4 in Example 1.

As seen in FIG. 10A, the signal from probe Erec was lower than the signal from probe Bact when analysing RNA from *C. symbiosum* E1051. This was due to the lower level of fluorophore labeling of probe Erec as compared to probe Bact. The level of fluorophore labeling of probes Bact and Chis were equal and hence, the signal intensity from probes Bact and Chis were equal when analysing RNA from *C. tyrobutyricum* E908. Thus, the level of probe labeling could be used to adjust the detection limit to an adequate level. In qualitative analysis of microbial population comprising of RNA from *C. tyrobutyricum* E908, *C. symbiosum* E1051 and *C. lituseburense* E1853 signal all probes Bact, Chis and Erec gave a signal, as expected. Bact probe identified all strains, whereas Chis identified only strain E908 and Erec identified only strain E1051.

As seen in FIG. 10B probes Bact and Chis, which have equal level of fluorophore labeling could be used to quantify the relative proportion of bacteria belonging to the *C. histolyticum* group (*C. tyrobutyricum* E908) in a mixed bacterial population (*C. tyrobutyricum* E908 and *C. symbiosum* E1051). Bact probe identified both strains, whereas Chis identifies only strain E908.

EXAMPLE 5

Detection and Quantification of 16S rRNA Targeted Probes by Mass Spectrometry

The relative proportion of 16S rRNA targeted probes Bact (Amann R. I., et al., Appl. Environ. Microbiol. 56:1919-

1925, 1990) and Chis (Franks, A. H., et al., Appl. Environ. Microbiol. 64:3336-3345, 1998) in a sample was quantified by using mass spectrometry. The experimental set-up mimics a situation for probe detection where bacteria belonging to the *C. histolyticum*-group form a proportion of the total bacterial population. Probe Bact recognized all bacteria (previously eubacteria)(Amann R. I., et al., Appl. Environ. Microbiol. 56:1919-1925, 1990), whereas probe Chis recognized bacteria belonging to the group of *Clostridium histolyticum* (Franks, A. H., et al., Appl. Environ. Microbiol. 64:3336-3345, 1998). The experiment followed the steps set forth below:

Preparative Steps:

Step 1—Probes 16S rRNA targeted oligonucleotide probes Bact and Chis previously described in preparative step 1 in Example 1 and preparative step 1 in Example 2 were used in the experiment.

Step 2—Preparation of Analytes

A sample containing 1 µM of probe Bact and 0.1 µM of probe Chis was prepared.

Analytical Steps:

Step 1—Detection and Quantification of Probes by Mass Spectrometry

The sample containing Bact and Chis probes were analysed by using matrix-assisted desorption/ionisation time-of-flight mass spectrometry (MALDI-TOF MS) according to the instrument manufacturer's instructions (Sequenom). The probes were identified according to their mass and their relative amount in the sample quantified by the signal intensity (peak height).

As seen in FIG. 12 the probes Bact and Chis could be identified as individual peaks in mass spectrometry. Probe Chis was represented by two peaks, because the probe had two different sequences (sixth base from the 3' end is either C or T), which consequently had distinct masses. The signal of Bact probe was approximately ten times higher that the combined signal from the two peaks from the probe Chis. The signal intensities of the probes correlated well with their relative proportion in the sample.

EXAMPLE 6

Quantitative and/or Comparative Assessment of Variations in Polynucleotide Amounts in Cell or Tissue Samples Using Biotinylated Oligo (dT)

Preparative Steps:

Genomic DNA and oligonucleotides were used to create specific probes of distinctive sizes.

Step 1.—Preparing Genomic DNA

*Saccharomyces cerevisiae* VTT-H1346 (wt) cells were grown, harvested and genomic DNA was isolated from cells as described in Supplement 39, *Current Protocols in Molecular Biology* (1997) 13.11.1-13.11.4, John Wiley & Sons. Inc.

Step 2.—Designing and Preparing Primers

Specific probe sequences for a set of genes were obtained using methods and computer program described in Kivioja et al, Bioinformatics, 2002 July; 18 Suppl 1:S199-206 (probes for *S. cerevisiae* genes YAL054c-ACS1, YCR005c-CIT2, YMR083w-ADH3 and YBL015w-ACH1) or by using the programs: EBI Genomes Server (2001) at http://www.ebi.ac.uk/genomes/. for downloading coding sequences (CDS) form *S. cerevisiae* genome; Steve Rozen, Helen J. Skaletsky (1998) Primer3. Code available at http://www-genome.wi.mit.edu/genome_software/other/primer3.html. for finding unique primers in CDSs and http://www.ncbi.nlm.nih.gov/BLAST/ for checking uniqueness for primers and in silico prepared products in genome/CDS (probe for *S. cerevisiae* gene YFL039c-ACT1).

The forward and reverse primer sequences obtained were (in direction 5'-3')

| | | |
|---|---|---|
| YAL054c-ACS1: | | |
| ACAATGCCAGGGTTTGACAATG | (SEQ ID NO:5) | |
| and | | |
| AAAGACATCGGGCCATTTGC, | (SEQ ID NO:6) | |
| YCR005c-CIT2: | | |
| TTAGCACGCCCATGAAGTGG | (SEQ ID NO:7) | |
| and | | |
| AGGATGAAGATTTCGTGGACTTGA, | (SEQ ID NO:8) | |
| YMR083w-ADH3: | | |
| AAGCTACCAAAGGTGGCCCTC | (SEQ ID NO:9) | |
| and | | |
| AGGCTTCTCTCGTATCAGCTCTGT, | (SEQ ID NO:10) | |
| YBL015w-ACH1: | | |
| GCCCTCTGACGACATGTCCAG | (SEQ ID NO:11) | |
| and | | |
| ATTGGCGTGCGCGTAAATGT | (SEQ ID NO:12) | |
| and | | |
| YFL039c-ACT1: | | |
| GCCCCAGAAGAACACCCTGT | (SEQ ID NO:13) | |
| and | | |
| ACCGGCCAAATCGATTCTCA | (SEQ ID NO: 14) | |
| correspondingly. | | |

To each primer pair obtained for a certain gene, so called universal primer sequences were attached to forward and reverse primers. 5'-tgctaggcgcgccgtc-3' (SEQ ID NO:15) sequence to forward primer and 5'-ggatgcggccgctctc-3' (SEQ ID NO:16) sequence to reverse primer of the primer pair. Thus e.g. for gene YBL015w-ACH1 full length forward primer was (SEQ ID NO: 17)
5'-tgctaggcgcgccgtcGCCCTCTGACGACATGTCCAG-3' and full length reverse primer was (SEQ ID NO:18)
5'-ggatgcggccgctctcATTGGCGTGCGCGTAAATGT-3'.

The final sizes of the probes produced by using polymerase chain reaction (PCR) with primers containing both specific and universal sequences were the following:

YAL054c-ACS1: 193 bases;
YCR005c-CIT2: 207 bases;
YMR083w-ADH3: 248 bases;
YFL039c-ACT1: 290 bases; and
YBL015w-ACH1: 453 bases Primers consisting of universal and specific parts were purchased from Sigma-Genosys Ltd. Universal primers, 5'-tgctaggcgcgccgtc-3' (SEQ ID NO:15) and 5'-ggatgcggccgctctc-3' (SEQ ID NO:16), with 5'-attached 6FAM™ fluorophore were purchased from ThermoElectron Corporation.

Step 3.—Preparing Probes

A PCR reaction was performed to amplify the specific probe sequences from the genomic DNA (from step 1). The buffer conditions were adjusted to the requirements of the used thermostable, proofreading (3'-5' exonuclease activity) DNA polymerase. A PCR program consisting of 98° C., 30 s; 10 cycles of 98° C. 10 s, 70° C. 20 s (−0.5° C./cycle), 72° C. 25 s; 20 cycles of 98° C. 10 s, 65° C. 20 s, 72° C. 25 s; 72° C. 10 min was used.

Subsequently the PCR reactions were purified using QIAquick PCR Purification Kit Protocol (QIAquick® Spin Handbook, March 2001; QIAGEN). The probe fragments were run in 2.5-4% agarose gels (stained with ethidium bromide) in horizontal gel electrophoresis at 75 V for 1-2 h, isolated and further purified using QIAquick Gel Extraction Kit Protocol (QIAquick® Spin Handbook, March 2001; QIAGEN).

Fluorescent label was introduced to the probes during a second PCR reaction. Universal primers with 5'-attached fluorophores, 6FAM™, were used to amplify the purified probes under conditions essentially similar to those described above. Subsequently the PCR reactions were purified using QIAquick PCR Purification Kit Protocol (QIAquick® Spin Handbook, March 2001; QIAGEN). The probes were then analysed on a capillary electrophoresis DNA sequencer ABI PRISM® 310, Genetic Analyser (Applied Biosystems) using GeneScan® Analysis Software (Applied Biosystems). The probe samples were diluted to appropriate concentration and mixed with a known amount of GeneScan-500 Size Standard (Applied Biosystems) and formamide was added to obtain suitable injection volume.

Agilent 2100 Bioanalyzer® and DNA 500 LabChip Kit (# 5064-8284, Agilent) was used to monitor the quality and quantity of the purified products after each PCR.

The preparation of probes by PCR is depicted in FIG. 13

Step 4.—Preparing the RNA Analytes

S. cerevisiae VTT-H2217 cells were grown on yeast nitrogen base (Difco, #291940) medium with essential amino acids (modification of Sherman et al. Methods in yeast genetics, Cold Spring Harbor Laboratory, 1983), and with 3% glucose, to O.D. 3.5-4.0 and the messenger RNA was isolated according to a downscaled protocol described in Promega Notes Magazine Number 41, p. 14, (1993). The yield and integrity of mRNA was checked using Agilent 2100 Bioanalyzer® and RNA 6000 Nano LabChip Kit (#5064-4476, Agilent).

The experiment followed the steps set forth below:

Analytical Steps:

Step 1—Assembling the Hybridization Assay.

The hybridization assays were assembled on a PCR plate (#AB-0600, Abgene) combining 2× hybridization solution: 1.2 M NaCl, 0.12 M sodium-citrate (pH 7), 0.2% (w/v) SDS, 40% formamide and 0.04% (w/v) Ficoll, 0.04% (w/v) polyvinylpyrrolidone, 0.04% (w/v) bovine serum albumin (2× Denhardt's solution); probe mixture (containing 100 fmol each 6FAM™ labeled probe); 200, 400 or 600 ng of mRNA (each amount in duplicates A and B); 3.5 fmol/(ng mRNA) of Biotinylated Oligo(dT) Probe (Z5261, Promega) and Rnase free water to dilute the hybridization solution to 1× in final volume. A typical final volume of an assay is 30-60 μL.

Step 2—Denaturation and Hybridization of Probes and Oligo (dT) to mRNA in Solution The PCR plate was sealed using peelable heat sealing foil (EASY Peel, AB-0745 Abgene and Thermosealer (AB-0384/240 Abgene). The assembled assay mixtures were incubated in a thermal block (DNA Engine™ PTC200, MJ Research) at 75° C. for 5 min, at 58° C. for 8 hrs and at 45° C. for 8 hours. Finally, the hybridization reactions were incubated at room temperature for 10 min (in order to hybridize the Biotinylated Oligo(dT) Probe to the mRNAs).

Step 3—Affinity Capture, Washes and Elution

Following the hybridization, KingFisher magnetic particle processor (ThermoLabsystems) was used to perform affinity capture, washes and elution step by moving streptavin coated magnetic particles from step to step on a KingFisher microtiter plate according to a programmed protocol. Solutions for each step were pipetted beforehand to specified wells in the microtiter plate and the procedure was carried out in room temperature.

The hybridization reactions from incubation wells were moved into specified wells in a KingFisher plate. In order to transfer the hybridization mixtures quantitatively into the KingFisher wells the incubation wells in step 2 were rinsed once with 1.5× hybridization volume of 0.5×SSC (0.075 M NaCl-7.5 mM sodium citrate, pH 6.5)-0.1% SDS solution and the rinsing solutions were added to the same KingFisher wells with the hybridization mixtures.

Biotinylated Oligo(dT): mRNA: probe-hybrids were collected on streptavidin coated magnetic particles (Streptavidin MagneSphere® Paramagnetic Particles, Z5241, Promega) for 30 min. Following capturing the particles were washes three times with 0.2×SSC-0.1% SDS and two times with 0.1×SSC-0.1% SDS and the probes were eluted with 30 μL of formamide. Subsequently, the formamide was evaporated in a lyophilisator and the probes were resuspended in 5 μL of water.

Step 4—Identification and Analyses of Eluted Probes

The eluted probes were analysed by using a capillary electrophoresis DNA sequencer ABI PRISM® 310, Genetic Analyser (Applied Biosystems) and GeneScan® Analysis Software (Applied Biosystems). The resuspended samples were mixed with a known amount of GeneScan-500 Size Standard (Applied Biosystems) and formamide was added to obtain suitable injection volume.

The eluted probes were identified based on their migration behaviour in the capillary electrophoresis, compared to the size standard and runs performed for single probes in the Preparative step 3 with same running conditions. The quantity of the eluted probes was determined according to the peak area (area units of fluorescence, AU). The result was read from the electropherogram and from the data file. The ratio of fluorescence (AU) from the probes YBL015w-ACH1 (size 453 bases) and YCR005c-CIT2 (size 207 bases) in all assays (mRNA amounts 200, 400 and 600 ng) was calculated (duplicates A and 1) as shown in Table 4, as well as the average and standard deviation of ratios in the six assays.

TABLE 4

The ratio of signals from probes YBL015w-ACH1 (size 453 bases) and YCR005c-CIT2 (size 207 bases) in assays A and B

| Amount of mRNA in assay (ng) | Assay A | Assay B | Average | Standard deviation |
|---|---|---|---|---|
| 200 | 4.7 | 4.5 | | |
| 400 | 5.5 | 4.6 | | |
| 600 | 6.0 | 6.1 | | |
| | | | 5.2 | 0.7 |

EXAMPLE 7

Quantitative Evaluation of Small Amounts of Analytes

Preparative Steps:

The preparative steps were performed as described in Example 6.

Analytical Steps:

The analytical steps of the probes differed from those in Example 6 as described below in the experimental design to detect very low amounts of RNA.

Step 1—Assembling the Hybridization Assay.

The hybridization assays were assembled as described in analytical step 1 in Example 6 (each mRNA amount 200, 400 and 600 ng in duplicates C and D).

Step 2—Denaturation and Hybridization of Probes and Oligo (dT) to mRNA in Solution The denaturation and hybridization were performed as described in analytical step 2 in Example 6.

Step 3—Affinity Capture, Washes and Elution

Affinity capture, washes and elution were performed as described in analytical step 3 in Example 6.

Step 4—Amplifying of Eluted Probes

The eluted probes (resuspended in 5 µl of water) were amplified using fluorophore labeled primers (described in Preparative step 2 in Example 6) in a PCR reaction. The buffer conditions were adjusted to the requirements of the used thermostable, proofreading (3'-5' exonuclease activity) DNA polymerase. A PCR program consisting of e.g. 98° C. 30 s; 15 cycles of 98° C. 10 s, 72° C. 30 s, was used. A negative control (without template) was performed using the same PCR program.

Step 5—Purification of the Amplified Probes

Subsequently the PCR reactions were purified using QIAquick PCR Purification Kit Protocol (QIAquick® Spin Handbook, March 2001; QIAGEN).

Step 6—Diluting of Purified Probes

The purified probes were diluted 1:100 in water. The negative control was not diluted.

Step 7—Identification and Analysis of Diluted Probes and Negative Control

The diluted probes were identified and analysed by using a capillary electrophoresis DNA sequencerABI PRISM® 310, Genetic Analyser (Applied Biosystems) and GeneScan® Analysis Software (Applied Biosystems) under same conditions as the eluted probes in analytical step 4 in Example 6. 0.5 µl of the diluted samples or 1 µl of non-diluted negative control was mixed with a known amount of GeneScan-500 Size Standard (Applied Biosystems) and formamide was added to obtain suitable injection volume.

The amplified and diluted probes were identified based in their migration behaviour in the capillary electrophoresis, compared to the size standard and runs performed for single probes in the Preparative step 3 with same running conditions. The quantity of the amplified and diluted probes was determined according to the peak area (AU). The result was read from the electropherogram and from the data file.

The electropherograms of assays assembled with 600 ng mRNA (Analytical Step 1) without amplification (Example 6) and with amplification and a negative control amplification are depicted in FIG. 14. In the non-amplified sample only the peak from the probe YCR005c-CIT2 (207 bases) can be clearly seen. In the amplified (and diluted) assays YCR005c-CIT2 could be seen as a strong peak and also peaks from probes YAL054c-ACS1 (193 bases) and YFL039c-ACT1 (size 290 bases) are clearly seen, as well as traces of peaks from probes gene YMR083w-ADH3 (248 bases). The negative control PCR showed no amplification of the probes at issue.

The ratio of the probe fluorescence (AU) from probes YBL015w-ACH1 (size 453 bases) and YCR05c-CIT2 (size 207 bases) in all amplified assays (mRNA amounts 200, 400 and 600 ng) was calculated (duplicates C and D) as shown in Table 5, as well as the average and standard deviation of ratios in the six assays. The average ratios of the two probes calculated from the amplified assays (Table 5) and from the non-amplified assays (Table 4) were well comparable taking into account that purification, dilution and inaccuracy in pipetting small volumes can bias the quantification.

TABLE 5

The ratio of signals from probes YBL015w-ACH1 (size 453 bases) and YCR005c-CIT2 (size 207 bases) in assays C and D after 15 cycles of PCR

| Amount of mRNA in assay (ng) | Assay C | Assay D | Average | Standard deviation |
|---|---|---|---|---|
| 200 | 3.5 | 3.8 | | |
| 400 | 4.6 | 4.4 | | |
| 600 | 3.8 | 4.5 | | |
| | | | 4.1 | 0.5 |

The invention claimed is:

1. A method for determination of amounts or relative proportions of more than one individual ribopolynucleotide sequence or subgroups thereof in a sample comprising a mixture of target ribopolynucleotide sequences using a quantitative affinity aided solution hybridization in combination with size- or mass-based fractionation for obtaining resolution, wherein the method comprises the consecutive steps of:

(a) providing, one or more pools with more than one soluble polynucleotide probe, wherein each probe in said pool is complementary to an individual target ribopolynucleotide sequence in the sample, being present in a molar excess as compared to the target ribopolynucleotide sequences, and has approximately the same number of hybridizing nucleotides, which are complementary to said target ribopolynucleotide sequences, wherein approximately the same number of nucleotides means that the polynucleotide probes are not distinguishable from each other in size- or mass-based separation, fractionation and recording and are made distinguishable by providing said polynucleotide probes with one or more resolution enabling tags, which tags are oligonucleotide residues, which change the mass or size of the polynuclotide probes and provide them with different mobilities in fractionation, separation or recording systems without disturbing the hybridization or capturing reaction, wherein each pool of polynucleotide probes are placed in their own vessels;

(b) providing a mixture of affinity tagged target ribopolynucleotide sequences by contacting the sample comprising the mixture of target ribopolynucleotide sequences with at least one affinity tag; and thereafter (c) performing steps (i) and (ii) simultaneously, or sequentially; in the order (i) and (ii), wherein steps (i) and (ii) comprise: (i) allowing a hybridization reaction to take place between the molar excess of polynucleotide probes from step (a) and the affinity tagged target ribopolynucleotide sequences from step (b) leading to formation of hybrids; (ii) providing captured hybrids by recovering the hybrids, on a separation aiding tool provided with an affinity pair of the affinity tag of the target ribopolynucleotide sequences;

(d) providing released polynucleotide probes by eluting the polynucleotide probes in an unmodified form from the captured hybrids, wherein said released polynucleotide probes are provided with tracer tags in step (a) or are tracer tagged after release in step (d) or during or after amplification after the release in step (d);

(e) separating the released polynucleotide probes by electrophoretic or chromatographic techniques or mass spectrometry and recording the amount or relative proportions of distinguishable polynucleotide probes, the amount of which corresponds to the amount of complementary target ribopolynucleotide sequences in the mixture of target ribopolynucleotide sequences in the sample.

2. The method according to claim 1, wherein for the determination of variations in the amounts or relative proportions of polynucleotide transcripts or their subgroups in an individual organism, the soluble polynucleotide probes are designed from species or group-specific ribopolynucleotide sequences hybridizing with selected conserved or hypervariable regions from intragenomic sequences specific for subgroups, species, subspecies of transcripts expressed in the organism.

3. The method according to claim 2, wherein the target ribopolynucleotide sequences isolated from the sample comprising a mixed target population are messenger RNA (mRNA).

4. The method according to claim 1, wherein for the determination of variations in the amounts or relative proportions of ribopolynucleotide sequences representing individual organisms or subpopulations thereof in a target population, the polynucleotide probes are designed from species or group-specific ribopolynucleotide sequences hybridizing with a selected conserved or hypervariable region from intragenomic sequences specific for and/or representing different phylogenetic levels allowing the identification of subgroups, species, subspecies within a mixed target population.

5. The method according to claim 4, wherein the target ribopolynucleotide sequences from the sample comprising the mixed target population are ribosomal RNA.

6. The method according to claim 1, wherein the tracer tags are recordable by fluorescence.

7. The method according to claim 1, wherein more than five polynucleotide probes are in the pool.

8. The method according to claim 1, wherein the amount of the individual, captured and released polynucleotide probes is recorded with a fully or partly automatic recording system.

9. The method according to claim 8, wherein the electrophoretic or chromatographic techniques are capillary electrophoresis.

10. The method according to claim 1 wherein the amount of polynucleotide probes, wherein the resolution enabling tags are oligonucleotide residues acting as primers, are released and subsequently amplified and tracer tagged during or after the amplification and thereafter recorded.

11. The method according to claim 10, wherein the primers comprise specific and universal parts.

12. The method according to claim 1, wherein the polynucleotide probes are selected from the group consisting of stable DNA fragments, synthetic or recombinant polynucleotide sequences, and modified polynucleotide sequences.

13. The method according to claim 1, wherein a comparative, quantitative assessment of variations in the amounts of individual target ribopolynucleotide sequences or organisms and subgroups thereof in a population or mixture of target ribopolynucleotide sequences is carried out by providing sets of test kits, at least one test kit for each sample to be compared, wherein each of said test kits are provided with identical pools comprising more than one.

14. The method according to claim 13, wherein each set of test kits is provided with a tracer tag, which is distinguishable by the emitted signal.

15. The method according to claim 13 for assessing hygienic conditions and epidemiologic situations, effects of external stimuli or treatment modalities on a microbial population, wherein a comparative assessment of variations in the amounts or relative proportions of more than one individual target ribopolynucleotide sequence or subgroups thereof in a sample from a population are determined by providing a set of identical test kits for each sample to be compared, wherein the samples are obtained before and after applying the external stimulus or treatment.

16. The method according to claim 1, wherein the steps of the method are performed on a test kit, which comprises one or more pools, with more than one soluble polynucleotide probe.

17. The method according to claim 1, wherein the pools comprising polynucleotide probes are placed in wells on a microtiter plate.

18. The method according to claim 1, wherein the number of soluble polynucleotide probes in the pool is more than ten.

19. The method according to claim 1, wherein the polynucleotide probes are tracer tagged in step (a).

20. The method according to claim 1, wherein the polynucleotide probes are tracer tagged after the release in step (d).

21. The method according to claim 1, wherein the released polynucleotide probes in step (d) are amplified and tracer tagged during or after amplification.

22. The method according to claim 1, wherein the tracer tag is a fluorophor.

* * * * *